United States Patent
Iida et al.

(10) Patent No.: US 10,242,836 B2
(45) Date of Patent: Mar. 26, 2019

(54) DEVICES HAVING AN ELECTRON EMITTING STRUCTURE

(71) Applicant: NANOX IMAGING PLC, Gibraltar (GI)

(72) Inventors: Koichi Iida, Okayama (JP); Hidenori Kenmotsu, Tokyo (JP); Jun Yamazaki, Aichi (JP); Hitoshi Masuya, Chiba (JP)

(73) Assignee: NANOX IMAGING PLC, Gibraltar (GI)

( * ) Notice: Subject to any disclaimer, the term of this patent is extended or adjusted under 35 U.S.C. 154(b) by 228 days.

(21) Appl. No.: 14/385,503

(22) PCT Filed: Mar. 14, 2013

(86) PCT No.: PCT/IB2013/052045
§ 371 (c)(1),
(2) Date: Sep. 16, 2014

(87) PCT Pub. No.: WO2013/136299
PCT Pub. Date: Sep. 19, 2013

(65) Prior Publication Data
US 2015/0092923 A1    Apr. 2, 2015

Related U.S. Application Data

(60) Provisional application No. 61/611,990, filed on Mar. 16, 2012, provisional application No. 61/747,455, filed on Dec. 31, 2012.

(51) Int. Cl.
*H01J 35/06* (2006.01)
*H01J 35/14* (2006.01)
(Continued)

(52) U.S. Cl.
CPC ......... *H01J 35/065* (2013.01); *G01N 23/046* (2013.01); *G01T 1/161* (2013.01);
(Continued)

(58) Field of Classification Search
CPC ................. H01J 35/065; H01J 35/14
(Continued)

(56) References Cited

U.S. PATENT DOCUMENTS

| | | | | |
|---|---|---|---|---|
| 5,528,103 A | * | 6/1996 | Spindt | H01J 3/022 313/309 |
| 5,552,659 A | * | 9/1996 | Macaulay | H01J 3/022 313/309 |

(Continued)

FOREIGN PATENT DOCUMENTS

| | | |
|---|---|---|
| CN | 102324350 | 1/2012 |
| CN | 202126987 | 1/2012 |

(Continued)

OTHER PUBLICATIONS

Toshinobu Miyoshi et al., Development of an X-ray HARP-FEA detector system for high-throughput protein crystallography, Journal of Synchrotron Radiation (2008) 15, 281-284.*

*Primary Examiner* — Allen C. Ho
(74) *Attorney, Agent, or Firm* — Alphapatent Associates Ltd.; Daniel J. Swirsky

(57) ABSTRACT

The disclosure relates to an image capture device comprising an electron receiving construct and an electron emitting construct, and further comprising an inner gap providing an unobstructed space between the electron emitting construct and the electron receiving construct. The disclosure further relates to an x-ray emitting device comprising an x-ray emitting construct and an electron emitting construct, said x-ray emitting construct comprising an anode, the anode being an x-ray target, wherein the x-ray emitting device may comprise an inner gap providing an unobstructed space between the electron emitting construct and the x-ray emitting construct. The disclosure further relates to an x-ray imaging system comprising an image capture device and an x-ray emitting device.

10 Claims, 21 Drawing Sheets

(51) Int. Cl.
  *G01N 23/046* (2018.01)
  *H01J 1/304* (2006.01)
  *H01J 29/46* (2006.01)
  *H01J 31/12* (2006.01)
  *G01T 1/161* (2006.01)
  *H01J 3/02* (2006.01)
  *H01J 3/14* (2006.01)

(52) U.S. Cl.
  CPC ............ *H01J 1/3042* (2013.01); *H01J 3/021* (2013.01); *H01J 3/027* (2013.01); *H01J 3/14* (2013.01); *H01J 29/467* (2013.01); *H01J 31/127* (2013.01); *H01J 35/14* (2013.01); *G01N 2223/204* (2013.01); *G01N 2223/419* (2013.01); *H01J 2235/068* (2013.01)

(58) Field of Classification Search
  USPC ............ 378/98.8, 122, 137, 138; 250/370.09
  See application file for complete search history.

(56) References Cited

U.S. PATENT DOCUMENTS

| | | | | |
|---|---|---|---|---|
| 5,587,623 | A | 12/1996 | Jones | |
| 5,635,789 | A | 6/1997 | Makishima et al. | |
| 5,677,539 | A * | 10/1997 | Apotovsky | G01T 1/241 250/370.01 |
| 5,892,321 | A | 4/1999 | Itoh et al. | |
| 5,905,264 | A * | 5/1999 | Shahar | H01L 27/14601 250/370.01 |
| 5,929,557 | A | 7/1999 | Makishima et al. | |
| 6,002,199 | A * | 12/1999 | Spindt | H01J 3/022 313/306 |
| 6,013,986 | A | 1/2000 | Knall et al. | |
| 6,028,313 | A * | 2/2000 | McDaniel | G01T 1/1642 250/338.4 |
| 6,031,250 | A * | 2/2000 | Brandes | H01J 1/3042 257/77 |
| 6,034,373 | A * | 3/2000 | Shahar | H01L 27/14676 250/338.4 |
| 6,259,765 | B1 * | 7/2001 | Baptist | H01J 35/14 378/122 |
| 6,333,968 | B1 * | 12/2001 | Whitlock | B82Y 10/00 378/122 |
| 6,456,691 | B2 * | 9/2002 | Takahashi | B82Y 10/00 378/122 |
| 6,553,096 | B1 * | 4/2003 | Zhou | A61B 6/4488 378/122 |
| 6,674,837 | B1 * | 1/2004 | Taskar | A61B 6/00 378/122 |
| 6,760,407 | B2 * | 7/2004 | Price | H01J 35/24 378/119 |
| 6,807,248 | B2 * | 10/2004 | Mihara | A61B 6/032 378/10 |
| 6,911,767 | B2 * | 6/2005 | Takai | B82Y 10/00 313/309 |
| 6,980,627 | B2 * | 12/2005 | Qiu | B82Y 10/00 378/122 |
| 7,082,182 | B2 * | 7/2006 | Zhou | A61B 6/032 378/10 |
| 7,085,351 | B2 * | 8/2006 | Lu | A61B 6/4021 315/169.3 |
| 7,085,352 | B2 * | 8/2006 | Dunham | A61B 6/032 313/373 |
| 7,158,102 | B2 * | 1/2007 | Hansen | G09G 3/22 345/75.2 |
| 7,192,031 | B2 * | 3/2007 | Dunham | A61B 6/032 378/122 |
| 7,227,924 | B2 | 6/2007 | Zhou et al. | |
| 7,323,692 | B2 | 1/2008 | Rowlands | |
| 7,348,531 | B2 | 3/2008 | Okuda et al. | |
| 7,548,018 | B2 * | 6/2009 | Lee | H01J 29/467 313/309 |
| 7,627,087 | B2 * | 12/2009 | Zou | H01J 1/304 378/122 |
| 7,696,680 | B2 * | 4/2010 | Wei | H01J 1/304 313/495 |
| 7,723,664 | B2 | 5/2010 | Honda et al. | |
| 7,781,738 | B2 * | 8/2010 | Nam | C09K 11/595 250/361 R |
| 7,801,277 | B2 * | 9/2010 | Zou | H01J 35/065 378/122 |
| 7,809,114 | B2 * | 10/2010 | Zou | H01J 1/3048 378/122 |
| 7,825,591 | B2 * | 11/2010 | Kimiya | H01J 1/46 313/310 |
| 7,826,594 | B2 * | 11/2010 | Zou | H01J 35/065 378/122 |
| 7,826,595 | B2 * | 11/2010 | Liu | H01J 35/065 378/122 |
| 7,834,308 | B2 | 11/2010 | Namba et al. | |
| 7,868,850 | B2 * | 1/2011 | Jin | G09G 3/22 315/169.3 |
| 7,873,146 | B2 * | 1/2011 | Okunuki | H01J 35/065 378/122 |
| 7,991,114 | B2 * | 8/2011 | Okunuki | A61B 6/032 378/122 |
| 7,991,120 | B2 * | 8/2011 | Okunuki | H01J 35/065 378/122 |
| 8,044,596 | B2 | 10/2011 | Taniguchi et al. | |
| 8,155,273 | B2 * | 4/2012 | Eaton | H01J 35/065 378/122 |
| 8,203,112 | B2 * | 6/2012 | Okuda | H01L 27/14609 250/208.1 |
| 8,270,567 | B2 | 9/2012 | Yamamoto et al. | |
| 8,274,205 | B2 * | 9/2012 | Wilson | H01J 1/3044 313/309 |
| 8,428,221 | B2 | 4/2013 | Boese et al. | |
| 8,447,013 | B2 | 5/2013 | Sprenger et al. | |
| 8,488,737 | B2 | 7/2013 | Boese et al. | |
| 8,488,742 | B2 * | 7/2013 | Tsujii | A61B 6/4441 378/138 |
| 8,503,614 | B2 * | 8/2013 | Legagneux | H01J 35/065 378/122 |
| 8,588,372 | B2 * | 11/2013 | Zou | H01J 35/065 378/113 |
| 8,755,493 | B2 * | 6/2014 | Travish | H01J 35/065 378/122 |
| 8,861,686 | B2 * | 10/2014 | Kim | G03B 42/02 378/149 |
| 8,953,747 | B2 * | 2/2015 | de Looz | H01J 35/14 313/402 |
| 8,989,351 | B2 * | 3/2015 | Vogtmeier | H01J 35/06 378/115 |
| 9,390,880 | B2 * | 7/2016 | Jeong | H01J 29/98 |
| 9,398,677 | B2 * | 7/2016 | Tang | H05G 1/32 |
| 9,666,401 | B2 * | 5/2017 | Park | H01J 3/021 |
| 9,711,255 | B2 * | 7/2017 | Kato | C09K 11/55 |
| 9,728,367 | B2 * | 8/2017 | Park | H01J 35/06 |
| 9,748,071 | B2 * | 8/2017 | Guerrera | H01J 37/073 |
| 9,775,225 | B2 * | 9/2017 | Tamura | A61B 6/032 |
| 9,793,089 | B2 * | 10/2017 | Plettner | H01J 37/153 |
| 9,922,793 | B2 * | 3/2018 | Hori | H01J 29/46 |
| 9,966,230 | B1 * | 5/2018 | Chuang | H01J 37/3177 |
| 10,068,740 | B2 * | 9/2018 | Gupta | A61B 6/40 |
| 2003/0044519 | A1 | 3/2003 | Takai | |
| 2003/0201954 | A1 | 10/2003 | Hansen et al. | |
| 2007/0235772 | A1 | 10/2007 | Jin et al. | |
| 2007/0246789 | A1 | 10/2007 | Freudenberger et al. | |
| 2008/0043920 | A1 | 2/2008 | Liu | |
| 2008/0135766 | A1 | 6/2008 | Nam et al. | |
| 2008/0211401 | A1 | 9/2008 | Nakada et al. | |
| 2009/0096393 | A1 | 4/2009 | Taniguchi | |
| 2009/0185660 | A1 | 7/2009 | Zou et al. | |
| 2010/0025568 | A1 | 2/2010 | Okuda et al. | |
| 2010/0128845 | A1 | 5/2010 | Yamamoto | |

(56) References Cited

U.S. PATENT DOCUMENTS

2010/0290593 A1    11/2010   Legagneux et al.
2011/0305314 A1    12/2011   Kitamura et al.

FOREIGN PATENT DOCUMENTS

| GB | 1467487 A | 3/1977 | |
|----|-----------|--------|--|
| JP | H07-29507 A | 1/1995 | |
| JP | H10 302688 A | 11/1998 | |
| JP | 2000-48743 A | 2/2000 | |
| JP | 2007194014 A | 8/2007 | |
| JP | 2007 305337 A | 11/2007 | |
| JP | WO2008/136188 A1 * | 11/2008 | ............ G01T 1/246 |
| JP | 2009-272289 | 11/2009 | |
| JP | 2011 071022 A | 4/2011 | |
| JP | 4693884 B2 | 6/2011 | |
| JP | 5041875 B2 | 10/2012 | |
| JP | 5066392 B2 | 11/2012 | |
| JP | 5294653 B2 | 9/2013 | |
| WO | 1997023002 | 6/1997 | |
| WO | 2013149004 A1 | 10/2013 | |

* cited by examiner

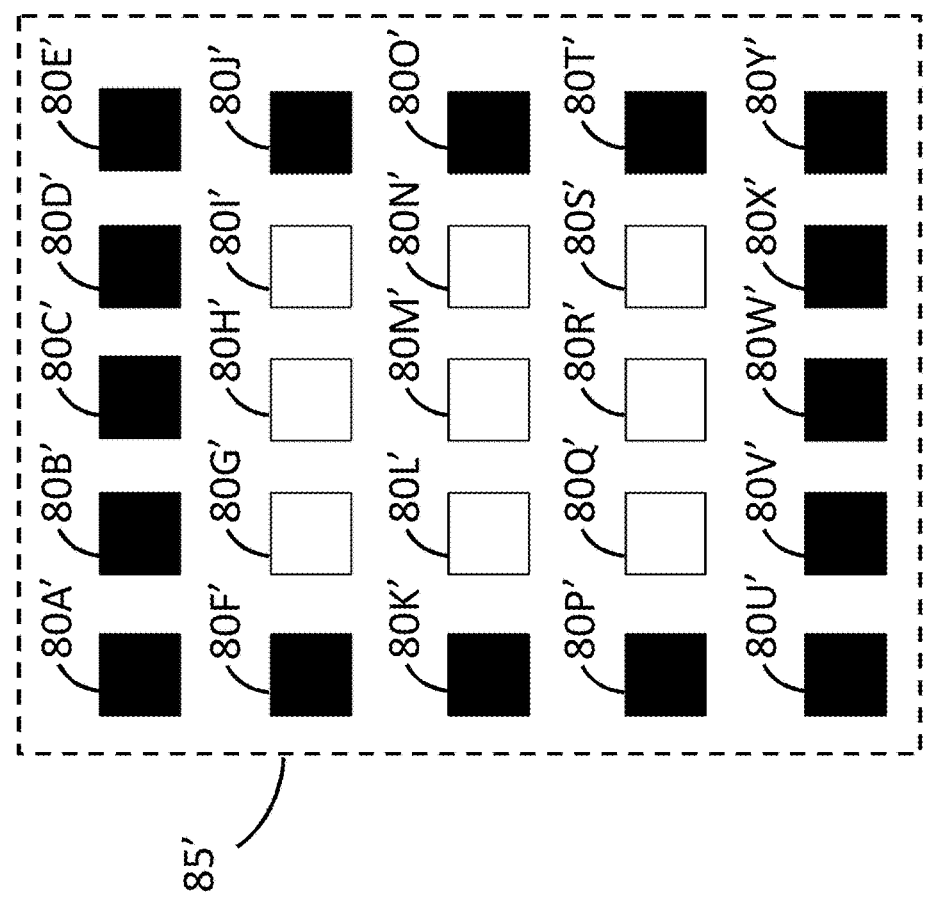

DEVICES HAVING AN ELECTRON EMITTING STRUCTURE

CROSS-REFERENCE TO RELATED APPLICATIONS

This application is a U.S. National Phase Application under 35 U.S.C. 371 of International Application No. PCT/IB2013/052045, which has an international filing date of Mar. 14, 2013, and which claims priority and benefit from U.S. Provisional Patent Application 61/611,990, filed Mar. 16, 2012 and U.S. Provisional Patent Application 61/747,455, filed Dec. 31, 2012, the contents and disclosures of which are incorporated herein by reference in their entirety.

FIELD OF THE INVENTION

The embodiments disclosed herein relate to a field emission type electron source and devices comprising the same, in particular, an image capture device and an x-ray emitting device.

BACKGROUND

There is a gaining enthusiasm for smaller and thinner (flat) imaging devices based on replacing hot cathode ray tube electron sources used in video tubes and X-ray imaging devices with field emission type electron sources. Examples of image capture devices using field emission type electron sources are visible light image capture devices as shown in, e.g., Japanese laid open publication JP 2000-48743A (the '743 publication) and X-ray image capture devices as shown in, e.g., Japanese laid open publication 2009-272289 (the '289 publication).

Video tubes using hot cathode electron sources, such as those shown in, e.g., Japanese laid-open publication JP H07-29507A (the '507 publication) as well as the above-mentioned prior art imaging devices comprising field emission type electron sources have typically made use of a grid electrode, e.g., a thin material with an array of small openings and having a grid-, mesh- or sieve-like structure, positioned between the anode and cathode. This grid electrode may also be referred to as a control grid or a trimming electrode. The grid electrode is typically for accelerating electrons from a hot cathode or a field emission type electron source and project the electron beam. The grid electrode may also improve the aim of electron beams by only allowing the passage of electron beams traveling orthogonally from the electron source and blocking electron beams having an angular component.

Reference is now made to FIG. 1, which shows a conventional, PRIOR ART image capture device with a field emission type electron source 15 and a grid electrode 20, as shown in the '743 publication. The grid electrode 20, positioned between the electron emitting construct (comprising the field emission type electron source 15) and the electron receiving construct (comprising the faceplate 3), accelerates and directs the electron beams from the field emission type electron sources 15 to a predetermined target area on the electron receiving construct.

Imaging devices comprising a grid electrode have the disadvantage of having a reduced utilization efficiency of the electron beams being emitted from the electron source. For example, when a grid electrode, e.g., as illustrated in the '507 publication, is used, electrons that fail to pass through the open area are absorbed into the grid and are lost without providing signal current. On the other hand, if the size of the grid electrode openings is widened (to increase utilization efficiency of the electron beams), another problem arises wherein electrons with an angular (i.e., non-perpendicular) component will pass through and hit the photoconductor outside of the predetermined target location. As such, electron beams may hit an adjacent pixel causing a readout in a pixel that is different from the target pixel, thus reducing image quality (e.g., resolution). In addition, the physical strength of the grid electrode become weaker as the aperture of the grid openings becomes wider. Therefore, it is difficult to assemble and maintain a grid with a large aperture. For at least these reasons, the ability to mitigate the reduced utilization efficiency of the electron beam caused by the grid electrode, by modifying the grid electrode, is limited.

Further, the grid electrode can become a source of microphonic noise in applications where the system must be moved during irradiation such as video imaging, CT scanning or Fluoroscopy. The interaction between the electron beam and the grid can create an energy spread in the electron beam, thus changing the system characteristics.

Finally, the presence of a grid electrode presents an assembly problem regardless of the grid opening aperture. This assembly problem is exacerbated in a large, thin imaging device such as a flat panel-type image capture device, in which the grid electrode must be assembled within a narrow gap in a precise manner, leading to increased defective products and increased cost of production.

The disclosure below addresses the above-described problems associated with conventional imaging devices using field emission type electron sources.

Further, there is a gaining enthusiasm for x-ray emission devices based on field emission type electron sources. However, enabling such devices to have the desired functional parameters is challenging. Earlier attempts at such devices, in particular the electron emitting component for such devices, have been deficient for various reasons, e.g., the electron sources cannot emit electron beams of sufficient flux density, the electron beams cannot be focused to the desired spot size, and the electron sources (and thus the devices themselves) have a short lifespan, poor stability and poor uniformity.

The disclosure below addresses the above-described problems associated with x-ray emission devices based on field emission type electron sources.

SUMMARY OF THE EMBODIMENTS

In a first aspect of the disclosure, the embodiments described herein provide an image capture device comprising an electron receiving construct and an electron emitting construct separated by at least one spacer situated such that an inner gap is present between said electron receiving construct and said electron emitting construct. The electron receiving construct may comprise a faceplate, an anode and an inward facing photoconductor. The electron emission construct may comprise: (a) a backplate, (b) a substrate, (c) a cathode, (d) a plurality of field emission type electron sources arranged in an array, wherein said field emission type electron source is configured to emit an electron beam towards said photoconductor and (e) a gate electrode. The inner gap may provide an unobstructed space between the electron emitting construct and the electron receiving construct.

In certain embodiments of the disclosure, the image capture device does not comprise a grid electrode.

In certain embodiments of the disclosure, the electron emitting construct may further comprise a plurality of first focus structures arranged in an array, each of said first focus structures comprising a first focus electrode.

In certain embodiments of the disclosure, the first focus structure may surround a unit cell comprising a subset of said field emission type electron sources, said unit cell defining a pixel.

In certain embodiments of the disclosure, the electron emission construct may further comprise a plurality of second focus structures arranged in an array, each of said second focus structures comprising a second focus electrode.

In certain embodiments of the disclosure, the photoconductor comprises amorphous Selenium.

In certain embodiments of the disclosure, the field emission type electron source is a Spindt-type electron source.

In certain embodiments of the disclosure, the image capture device comprises a resistive layer situated between the field emission type electron source and the cathode.

In certain embodiments of the disclosure, the field emission type electron source is electrically connected to a driving circuit via a signal line, and the first focus electrode surrounds said signal line.

In certain embodiments of the disclosure, the substrate is silicon based.

In certain embodiments of the disclosure, at least one member selected from the group consisting of the cathode, the resistive layer, the signal line, the field emission type electron source, the gate electrode, the first focus structure, the first focus electrode and any combination thereof, is integral to the substrate.

In certain embodiments of the disclosures, the pixel has the pixel pitch of 100 micrometers×100 micrometers or less.

In certain embodiments of the disclosure, the distance between the array of field emission type electron sources and the anode is between 50 micrometers and 400 micrometers.

In certain embodiments of the disclosure, the distance between the array of field emission type electron sources and the anode is 0.5 to 4.0 times the pixel pitch.

In a second aspect of the disclosure, the embodiments described herein provide an x-ray emitting device comprising an x-ray emitting construct and an electron emitting construct separated by at least one spacer situated such the x-ray emitting construct and the electron emitting construct face each other, and that an evacuated inner gap is present between said electron receiving construct and said electron emitting construct; said x-ray emitting construct comprising an anode, the anode being an x-ray target; and said electron emitting construct comprising at least one active zone, each active zone comprising at least one active area comprising: a cathode; a gated cone electron source, comprising a plurality of emitter tips arranged in an array; a resistive layer situated between the gated cone electron source and the cathode; a gate electrode comprising a plurality of gate holes, the position of at least one of said gate holes corresponding to the position of at least one of said emitter tips; wherein said emitter tip is configured to emit an electron beam towards the x-ray emitting construct.

In certain embodiments of the disclosure, the diameter of the gate hole is less than 200 nanometers.

In certain embodiments of the disclosure, the width of the base of the emitter tip is less than 300 nanometers.

In certain embodiments of the disclosure, the active zone comprises more than one active area.

In certain embodiments of the disclosure, the gate electrode is connected to a voltage source through a gate interconnect lead, the gate electrode being situated in a gap of the gate interconnect lead such that the gate electrode is connected on all sides to the gate interconnect lead. Optionally, the gate interconnect lead is thicker than the gate electrode.

In certain embodiments of the disclosure, the gate interconnect lead is of a thickness between 0.5 microns and 20 microns. In certain embodiments of the disclosure, the resistive layer is of a thickness greater than 300 nm or between 300 and 5000 nanometers.

In certain embodiments of the disclosure, the resistive layer comprises SiCN. Optionally, the resistive layer further comprises a first barrier sublayer situated at the interface with the cathode, a second barrier sublayer situated at the interface with the gated cone electron source, or both first and second barrier sublayers. Optionally, the barrier sublayer comprises SiCN or SiC having a silicon atomic percentage of less than 40%, or comprises amorphous carbon.

In certain embodiments of the disclosure, the gated cone electron source is capable of passing an electrical current having a flux density of between 1 and 10 mA/mm$^2$.

In certain embodiments of the disclosure, the active area is of an area of between 100 square microns and 4 square millimeters.

In certain embodiments of the disclosure, the active area comprises between 1 and 10 emitter tips per square micron.

In certain embodiments of the disclosure, the cathode is of a thickness between 0.5 microns and 20 microns.

In certain embodiments of the disclosure, the position of each of the emitter tips, the corresponding gate hole, the cathode and the resistive layer overlap along the plane of the electron emitting construct.

In certain embodiments of the disclosure, the inner gap provides an unobstructed space between said electron emitting construct and said electron receiving construct.

In certain embodiments of the disclosure, the anode comprises one or more of the group consisting of molybdenum, rhodium and tungsten.

In certain embodiments of the disclosure, the substrate is silicon-based.

Optionally, at least one member selected from the group consisting of the gate electrode, the cathode, the resistive layer and the gated cone electron source is integral to the substrate.

In certain embodiments of the disclosure, the active zone is enclosed by at least one focus structure.

In certain embodiments of the disclosure, the active zone comprises a plurality of active areas and said plurality of active areas is configured to be co-activated.

In certain embodiments of the disclosure, the active zone comprises a plurality of active areas, and one or more subsets of said plurality of active areas are capable of being activated independently. Optionally, the total emission current of the active zone is capable of being tuned through the controlled activation of one or more of said active zones. Optionally, said subsets of the plurality of active areas are organized as concentric regions, such that the initial width of the electron beam is capable of being tuned through the controlled activation of one or more of said concentric regions.

In a third aspect of the disclosure, the embodiments described herein provide an x-ray imaging system comprising an image capture device as provided in the first aspect of the disclosure and further comprising an x-ray emitting device as provided in the second aspect of the disclosure.

BRIEF DESCRIPTION OF THE FIGURES

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the several selected embodiments may be put into practice. In the accompanying drawings:

FIGS. 9A-D are schematic diagrams of various embodiments of active areas within an active zone, being activated in various pattern.

DESCRIPTION OF THE SELECTED EMBODIMENTS

Image Capture Device

Figure 1:
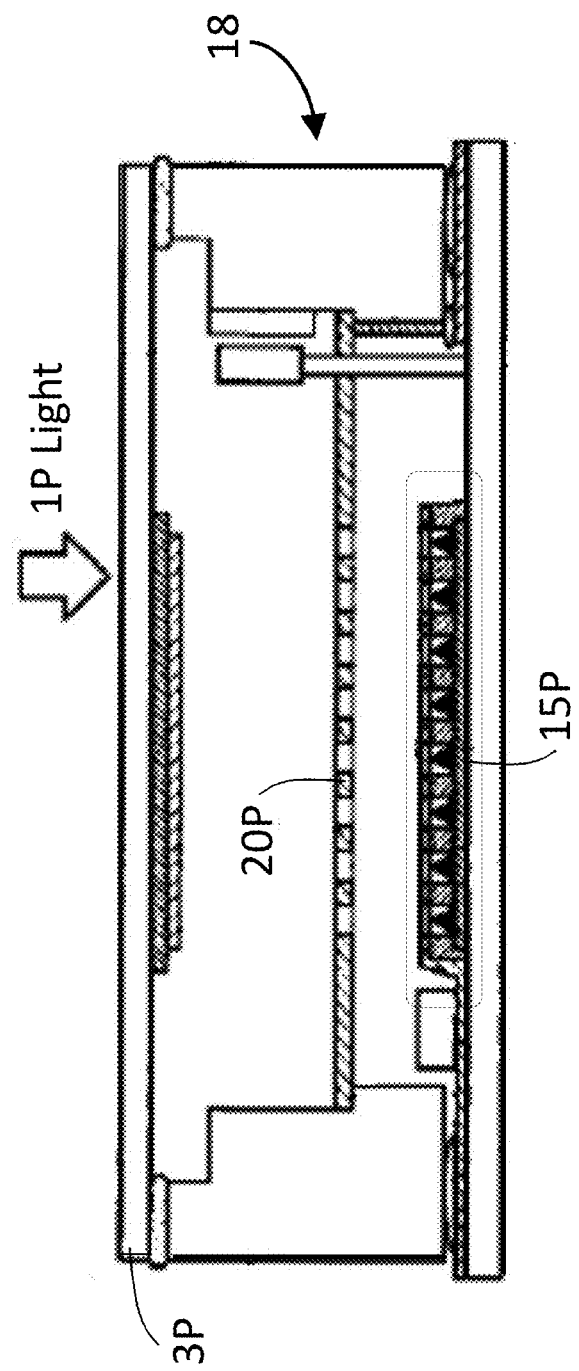
FIG. 1 is a schematic diagram representing a PRIOR ART image capture device comprising a grid electrode.
Figure 2:
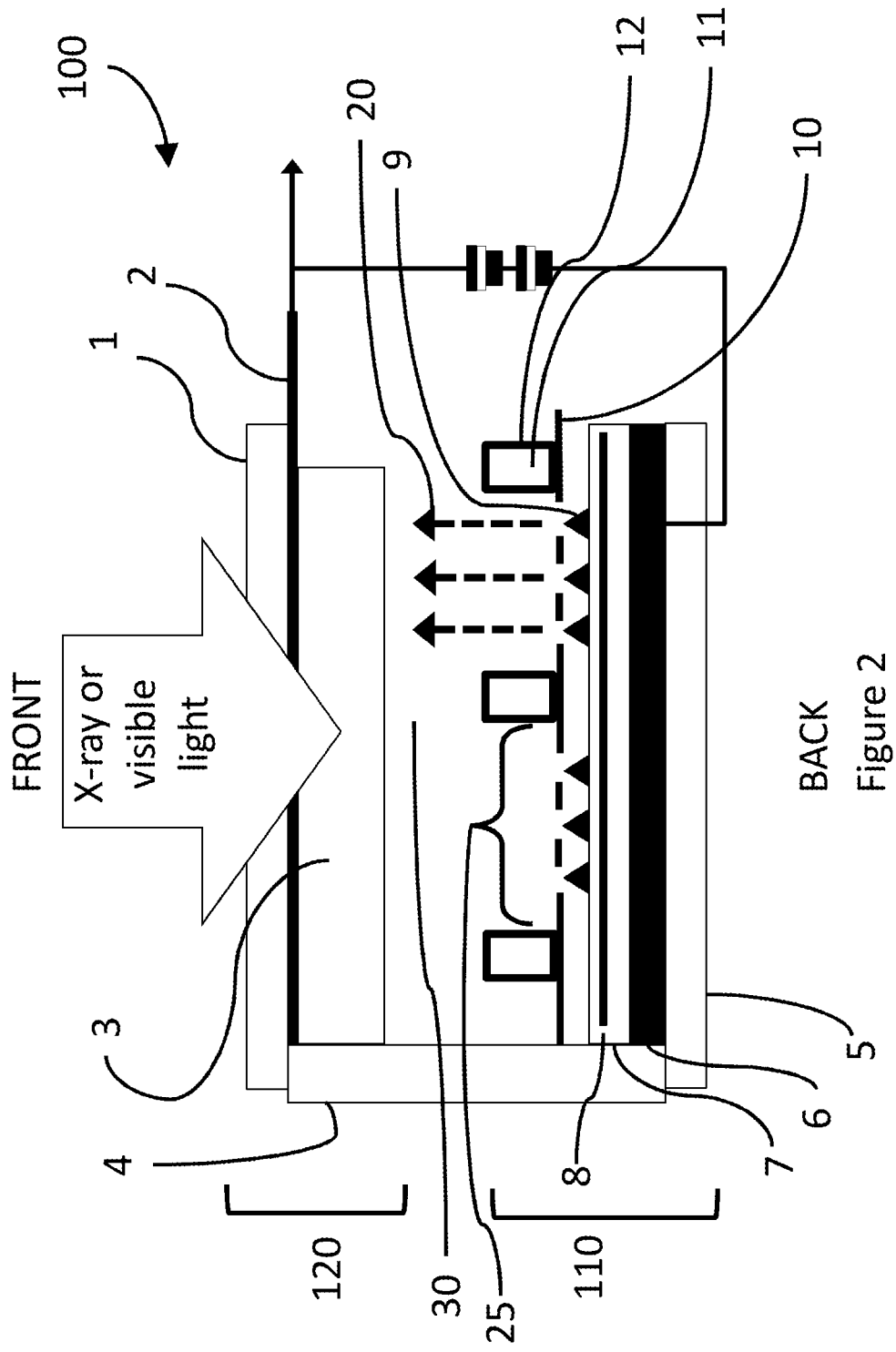
FIG. 2 is a schematic diagram representing an image capture device according to the present disclosure.
Figure 3:
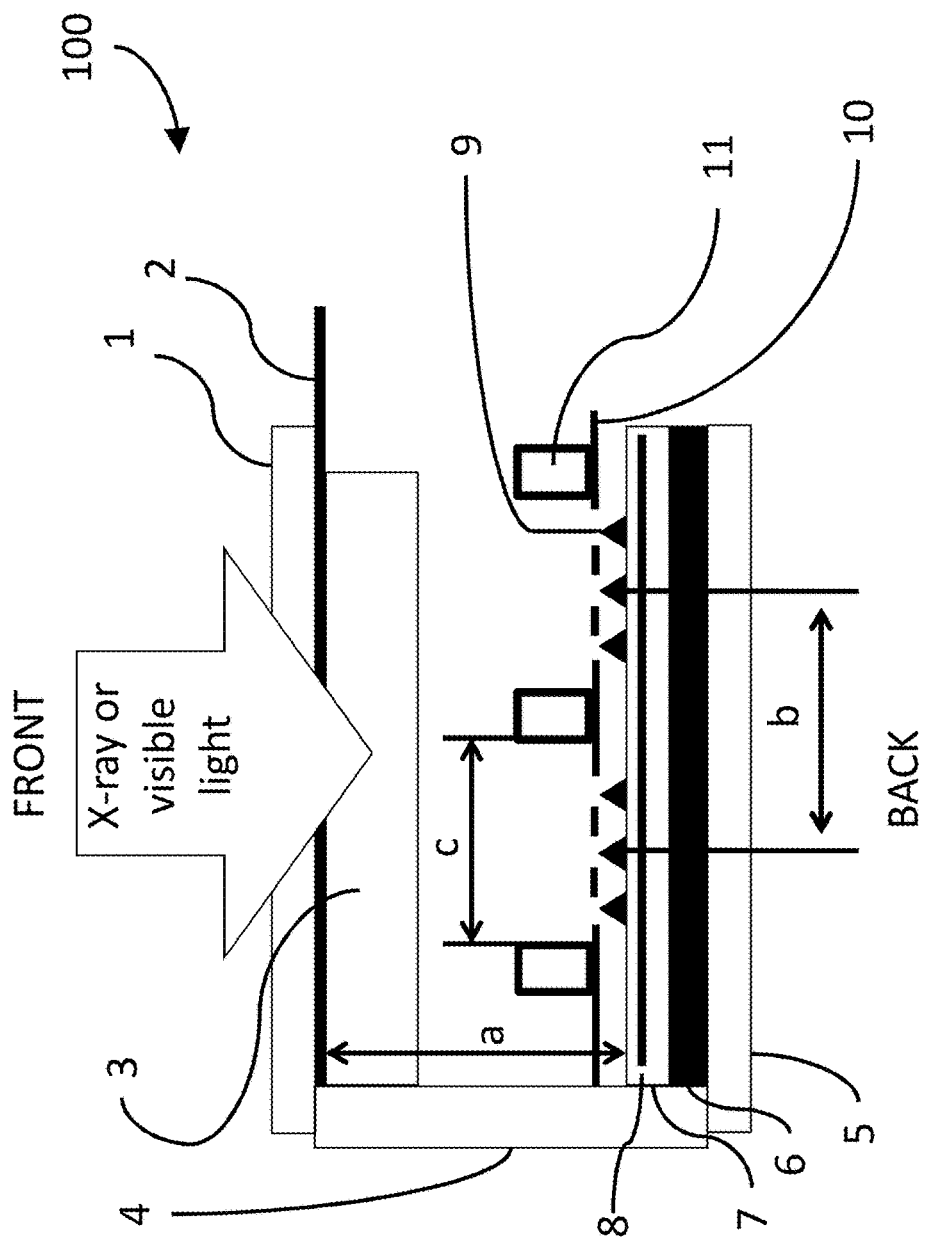
FIG. 3 is a schematic diagram representing the image capture device further indicating the device thickness a, the pixel pitch b and the pixel size c.
Figure 4:
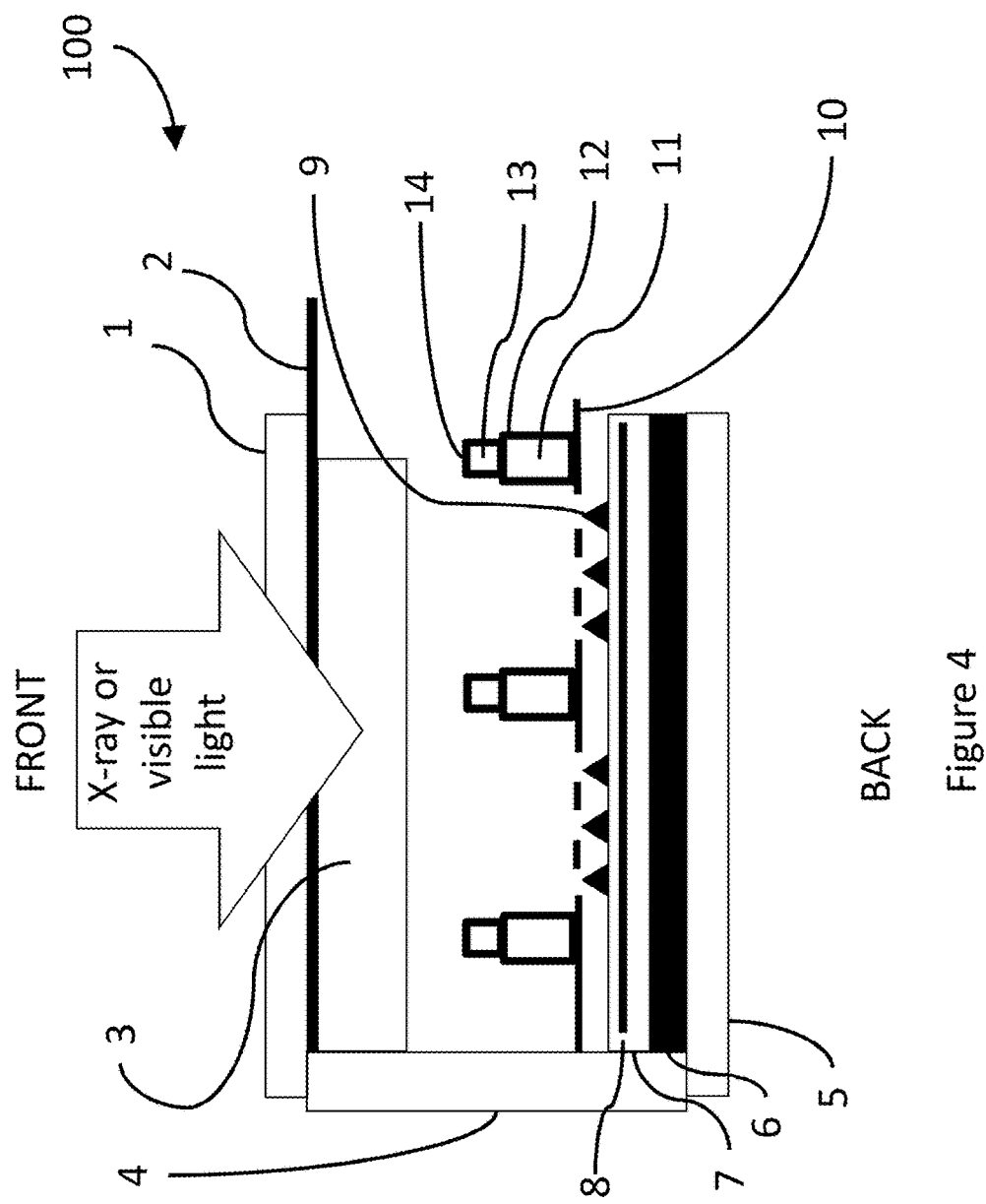
FIG. 4 is a schematic diagram representing the image capture device comprising an array of second focus structures.
Figure 5:
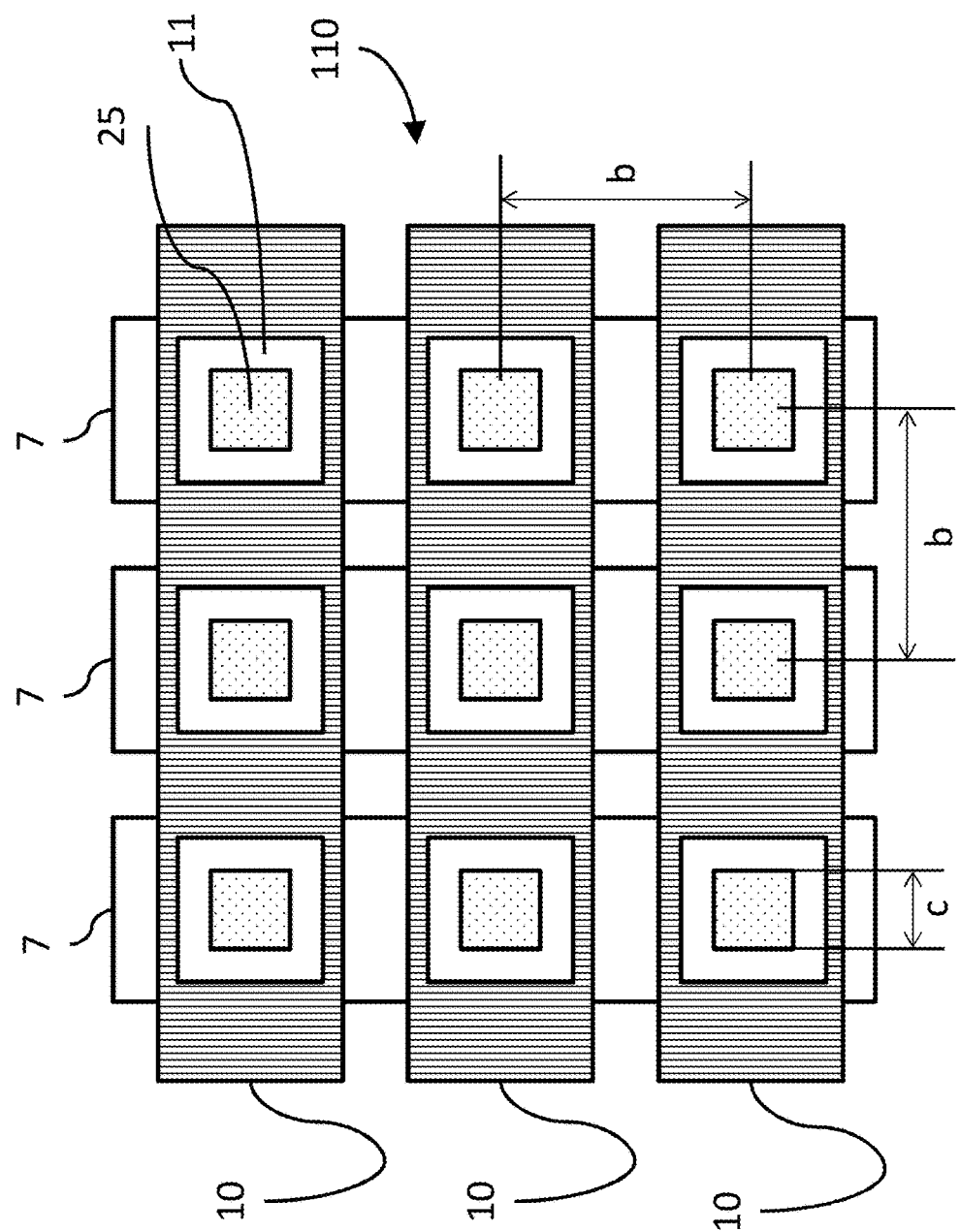
FIG. 5 is a schematic diagram representing an overhead view of the electron emitting construct.

Reference is now made to FIGS. 2-5, which shows an image capture device 100 of the disclosure. The image capture device 100 includes an electron emitting construct 110 and an electron receiving construct 120, separated by a spacer 4. The spacer 4 may be situated such that an inner gap 30 is present between the electron receiving construct 120 and the electron emitting construct 110. The inner gap 30 may be sealed and maintained under vacuum, and may provide an unobstructed space between the electron emitting construct 110 and the electron receiving construct 120.

It will be appreciated that the various options described for the electron emitting construct 110 and its components as described with reference to FIGS. 2-5 hereinbelow are options for the electron emitting construct 110 incorporated in the image capture device 100, as well as any other device incorporating an electron emitting construct described herein, including x-ray emission devices.

The electron emitting construct 110 may comprise a backplate 5, a substrate 6, a cathode 7, an array of field emission type electron sources 9 and a gate electrode 10. The electron receiving construct 120 may comprise faceplate 1, an anode 2 and an inward facing photoconductor 3.

The electron emitting construct 110 may further comprise a plurality of first focus structures 11 arranged in an array, each of said first focus structures 11 comprising a first focus electrode 12. In certain embodiments, the electron emitting construct 110 may further comprise a plurality of second focus structures 13 comprising a second focus electrode 14 (see FIG. 4).

The image capture device 100 may further comprise a resistive layer 8 (not shown) situated between the cathode 7 and the field emission type electron sources 9, in order to regulate the current into the field emission type electron sources 9.

The field emission type electron source 9 may be activated to emit an electron beam 20 that is directed towards the photoconductor 3. The field emission type electron source 9 is situated between the anode 2 and the cathode 7 such that the electron beam 20 emitted by the field emission type electron source 9 is accelerated towards the anode 2. The photoconductor 3 may be situated between the field emission-type electron source 9 and the anode 2, such that the emitted electron beam 20 strikes the photoconductor 3.

It is particularly noted that a grid electrode, which is generally situated in a prior art image capture device between the electron emitting construct 110 and the electron receiving construct 120, is not typically present in the image capture device 100 of the disclosure. A grid electrode may be a thin material with an array of small openings having a grid-, mesh- or sieve-like structure, positioned between the anode 2 and the cathode 7. The grid electrode may be referred to as a mesh electrode, a control grid or a trimming electrode. In the prior art system shown in FIG. 1, the grid electrode 20 lies between the electron emitting construct (comprising the field emission type electron source 15) and the electron receiving construct (comprising the faceplate 3). In contradistinction, with reference to FIG. 2, the inner gap 30 of the image capture device 100 of the disclosure provides an unobstructed space between the electron emitting construct 110 and the electron receiving construct 120, such that the electron beam 20 emitted from the field emission type electron source 9 travels directly to the photoconductor 3 without traversing any intermediate construction situated between the electron emitting construct 110 and the electron receiving construct 120.

The Electron Receiving Construct

With reference to FIGS. 2-5, the faceplate 1 and anode 2 of the electron receiving construct 120 may be constructed of materials and/or configured that transmits incident electromagnetic radiation radiating from the front of the faceplate 1, such that the incident electromagnetic radiation reaches the photoconductor 3. Materials used for the photoconductor 3 are known in the art, e.g., amorphous Selenium (a-Se), HgI$_2$, PHI$_2$, CdZnTe, or PbO. In a preferred embodiment, the photoconductor 3 comprises amorphous Selenium.

The electromagnetic radiation may be of any frequency. In certain embodiments, the electromagnetic radiation is in the X-ray frequency range. Alternatively, the electromagnetic radiation may be in the visible light frequency range.

The Substrate of the Electron Emitting Construct

With reference to FIGS. 2-5, the substrate 6 may be a semiconductor material, for example, crystallized silicon. Further, any one of the cathode 7, the resistive layer 8, the field emission type electron source 9, the gate electrode 10, the first focus structure 11, the first focus electrode 12, the second focus structure 13, the second focus electrode 14 and the signal line (not shown), or any combination thereof, may be processed on, and integral to, the substrate 6. In certain embodiments the resistive layer 8 may further be processed on, and integral to, the substrate 6.

The Field Emission Type Electron Source

With reference to FIGS. 2-5, the field emission type electron source 9 may be electrically connected to a driving circuit via a signal line (not shown) and further electrically connected to a gate electrode 10. The coordinated electrical activation of the driving circuit and the gate electrode 10 connected to a field emission type electron source 9 results in its activation, i.e., electron emission. The field emission type electron source 9 performs the electron emission by an electric field formed between the field emission type electron source 9 and the gate electrode 10. The field emission type electron source 9 may be a gated cone electron source having cones ("emitter tips") arranged in an array, each emitter tip being surrounded by an opening in the gate electrode 10 (a "gate hole"), a Spindt type electron source, a carbon nanotube (CNT) type electron source, a metal-insulator-metal (MIM) type electron source or a metal-insulator-semiconductor (MIS) type electron source. In a preferred embodiment, the field emission type electron source 9 may be a Spindt type electron source.

Anode and Cathode

With reference to FIGS. 2-5, the anode 2 and the cathode 7 are configured to generate an electrical field therebetween. This electrical field accelerates the electrons emitted from the field emission type electron source and directs them towards the photoconductor 3. The strength of the electric field between the anode 2 and the cathode 7 may be 0.1 to 2 volts per micrometers, 0.1 to 1.8 volts per micrometers, 0.1 to 1.5 volts per micrometers, 0.1 to 1 volts per micrometers, 0.1 to 0.5 volts per micrometers, about 0.1 volts per micrometers, about 0.2 volts per micrometers, about 0.3 volts per micrometers, about 0.4 volts per micrometers, about 0.5 volts per micrometers, about 0.6 volts per micrometers, about 0.7 volts per micrometers, about 0.8 volts per micrometers, about 0.9 volts per micrometers, about 1 volts per micrometers, about 1.2 volts per micrometers or about 1.5 volts per micrometers.

Focus Structures

With reference to FIGS. 2-5, a field emission type electron source 9 typically emits electrons having a range of trajectories, referred to as the divergence angle, and not all of the electrons are emitted orthogonal to the electron emitting construct 110. As such, a mechanism to correct the trajectory of the electrons, while minimizing the loss of electrons emitted at undesirable trajectories, is desired. The focus structures of the disclosure, e.g., first focus structure 11 comprising a first focus electrode 12 and second focus structure 13 comprising a second focus electrode 14, serve that function.

With reference to FIGS. 2-5, a first focus structure 11 may be configured to surround an emitter area 25, i.e., a unit cell comprising a subset of the plurality of field emission type electron sources 9. The emitter area 25 also defines a pixel size. The first focus electrode 12 may be configured to suppress scatter of the electron beams emitted from the corresponding emitter area 25 through the application of a first focus voltage, thus focusing the emitted electron beam.

In certain embodiments, the image capture device 100 of the disclosure may further comprise, in the electron emitter construct 110, an array of second focus structures 13 comprising a second focus electrode 14. Each second focus structure 13 may be adjacent and inward-facing in relation to each of the first focus structures 11 (with first focus electrodes 12), such that an electron emitting construct 110 comprises, in aggregate, a double focus structure facing the electron receiving construct 120. The second focus electrode 14 may be configured to further accelerate the electrons emitted from the corresponding emitter area 25 through the application of a second focus voltage, thus further focusing the emitted electron beam. It will be appreciated that the electron emitting construct 110 may comprise additional focus structures, resulting in an aggregate focus structure that is tripled, quadrupled, or the like.

The focus structures with the focus electrodes (e.g., first focus structure 11 with first focus structure 12 and/or second focus structure 13 with second focus structure 14) may further function as a drain for misdirected electrons. In certain embodiments, the first focus electrode 12 may be positioned to cover a signal line of the driving circuit for the field emission type electron source 9, thus reducing radiation noise in the signal lines by protecting the signal lines from irradiation by misdirected electrons.

Pixel Pitch and Device Thickness

As described above, and with reference to FIGS. 2-5, the first focus structure 11 may surround an emitter area 25, i.e., a unit cell comprising a subset of said field emission type electron sources 9. The subset of field emission type electron sources 9 within an emitter area 25 may define a pixel for the image capture device 100.

Pixel pitch is a specification of a pixel-based image capture device 100 that is known in the art. Pixel pitch may be expressed, e.g., as the distance between adjacent pixels. See, e.g., distance b in FIG. 3. Pixel size may be expressed as the area, width and length (if rectangular), or diameter (if circular) of, e.g. the emitter area 25. See, e.g., distance c in FIG. 3. Smaller pixel size and pixel pitch contribute to a finer resolution of the image that the device of the disclosure captures.

Another specification used in flat panel image capture devices is device thickness. The thickness of the image capture device 100 may be expressed as, e.g., the distance between a field emission type electron source 9 and the orthogonal position on the anode 2 (shown as distance a in FIG. 3). The thickness of the device may, alternatively, be expressed as the orthogonal distance between the anode 2 and the cathode 7, or as the orthogonal distance between any one component of the electron receiving construct 120 (e.g., the faceplate 1, the anode 2 or the photoconductor 3) and any one component of the electron emitting construct 110 (e.g., the field emission type electron source 9, the cathode 7, the substrate 6 and the backplate 5).

A discussed above, the image capture device 100 of the disclosure is designed to improve electron utilization efficiency of the image capture device 100, i.e., to increase the portion of electrons being emitted from the field emission type electron source 9 that strike the predetermined location on the photoconductor 3. As such, in the present disclosure, each emitter area 25 of the image capture device 100 (i.e., the cell comprising a plurality of field emission type electron sources 9 surrounded by a first focus structure 11) may require a lower density of electrons being emitted from the electron sources in order to achieve the same density of electrons striking the photoconductor 3, when compared to prior art image capture devices. Further, each emitter area 25 may thus require fewer field emission type electron sources and, thus, the pixel size, as well as the pixel pitch, of the image capture device 100 of the disclosure may be made smaller. The pixel of the image capture device 100 of the disclosure may be a square pixel with the pixel pitch of, e.g., between 10 micrometers and 1000 micrometers, between 50 micrometers and 200 micrometers, about 50 micrometers, about 75 micrometers, about 100 micrometers, about 125 micrometers, about 150 micrometers or about 200 micrometers. Preferably, the pixel of the image capture device 100 of the disclosure may be a square pixel with the pixel pitch of about micrometers 100 micrometers.

Typically, a thinner image capture device may be desired. However, thinner devices are more difficult to assemble, and the presence of a grid electrode exacerbates the difficulty in assembly. It is a particular advantage of the present disclosure that, because a grid electrode may not be used, the image capture device 100 of the disclosure may be made thinner, or the same thinness may be produced at less cost, when compared to prior art image capture devices that comprise a grid electrode.

Another specification of a flat panel image capture device 100 is the ratio between pixel pitch and device thickness. In the image capture device 100 of the disclosure, the device thickness, e.g., the distance between the cathode 7 and the anode 2, is from 0.5 to 4.0 times the pixel pitch. Expressed in an alternative fashion, the ratio between device thickness and pixel pitch (i.e., device thickness in micrometers/pixel pitch in micrometers) is between 0.5 and 4.0. Given the above ratio, if the pixel pitch is 100 micrometers, the gap between the cathode 7 and the anode 2 would be between 50 and 400 micrometers. In certain embodiments, the the device thickness, e.g., the distance between the cathode 7 and the anode 2, is from 0.5 to 2.0 times the pixel pitch, from 0.5 to 1.5 times the pixel pitch, from 1 to 3 times the pixel pitch, from 1 to 4 times the pixel pitch, about 0.5 times the pixel pitch, about 0.75 times the pixel pitch, about 1 times the pixel pitch, about 1.5 times the pixel pitch, about 1.75 times the pixel pitch, about 2 times the pixel pitch, about 2.25 times the pixel pitch, about 2.5 times the pixel pitch, about 2.75 times the pixel pitch, about 3 times the pixel pitch, about 3.25 times the pixel pitch, about 3.5 times the pixel pitch, about 3.75 times the pixel pitch or about 4 times the pixel pitch. The parameters of the field emission type electron source 9, the dimensions of the focus structures 11 (and 13), the voltage loaded to the focus electrodes 12 (and 14), and the height of the spacer 4, and other parameters of the device may be adjusted as needed.

X-Ray Emitting Device

Figure 6:
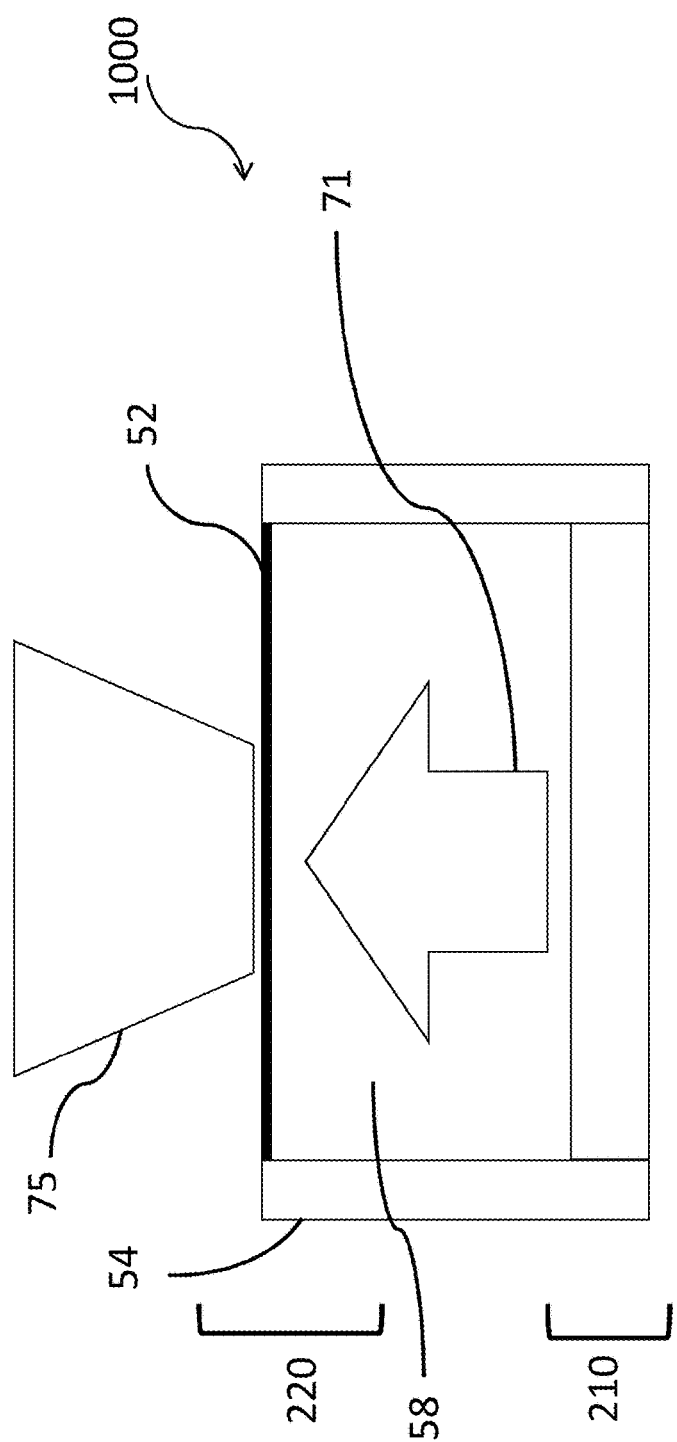
FIG. 6 is a schematic diagram representing a side view of an x-ray emitting device incorporating the electron emitting construct.

Reference is now made to FIG. 6, which shows an x-ray emitting device 1000 of the disclosure. The x-ray emitting device 1000 includes an electron emitting construct 210 and an x-ray emitting construct 220 (also referred to as an "electron receiving construct") facing each other, separated by at least one spacer 54. The spacer 54 may be situated such that an inner gap 58 is present between the x-ray emitting construct 220 and the electron emitting construct 210. The inner gap 58 may be sealed and maintained under vacuum, and may provide an unobstructed space between the electron emitting construct 210 and the x-ray emitting construct 220.

The electron emitting construct 210 may be activated to emit an electron beam 71 that is directed towards the x-ray emitting construct 220. A gated cone electron source incorporated into the electron emitting construct 210 is situated such that the emitted electron beam 71 is accelerated towards an anode 52 of the x-ray emitting construct 220.

The x-ray emitting construct 220 is situated to face the electron emitting construct 210, and includes an anode 52. The anode 52 of the x-ray emitting construct 220 and the cathode of the electron emitting construct 210 are configured to generate an electrical field therebetween. This electrical field accelerates the electrons emitted from the gated cone electron source and directs them towards the anode 52. Further, the anode 52 is capable of emitting x-rays 75 when struck with an electron beam 71. Anodes such as anode 52 are known in the art and may also be referred to as "targets" or "x-ray targets". The anode 52 may be constructed of, for example, molybdenum, rhodium, tungsten, or a combination thereof.

The X-ray emitting construct 220 may further include a collimator (not shown), on the outward facing side. Typically, the x-rays 75 are emitted in a range of directions, such that they radiate from the x-ray emitting construct 220 in a conical fashion. Collimators are devices that filter a stream of rays so that only those traveling parallel to a specified direction are allowed through. As such, the lateral spread of the emitted x-rays may be minimized or eliminated.

It is particularly noted that in prior art devices, a grid electrode has generally been situated between the electron emitting construct 210 and the x-ray emitting construct 220. A grid electrode may be a thin material with an array of small openings having a grid-, mesh- or sieve-like structure. The grid electrode may be referred to as a mesh electrode, a control grid or a trimming electrode. Such a grid electrode is typically not present in the x-ray emitting device 1000 of the disclosure. With reference to FIG. 6, the inner gap 58 of the x-ray emitting device 1000 of the disclosure provides an unobstructed space between the electron emitting construct 210 and the x-ray emitting construct 220, such that the emitted electron beam 71 travels directly to the x-ray emitting construct 220 without traversing any intermediate construction situated between the electron emitting construct 210 and the x-ray emitting construct 220.

Figure 7:
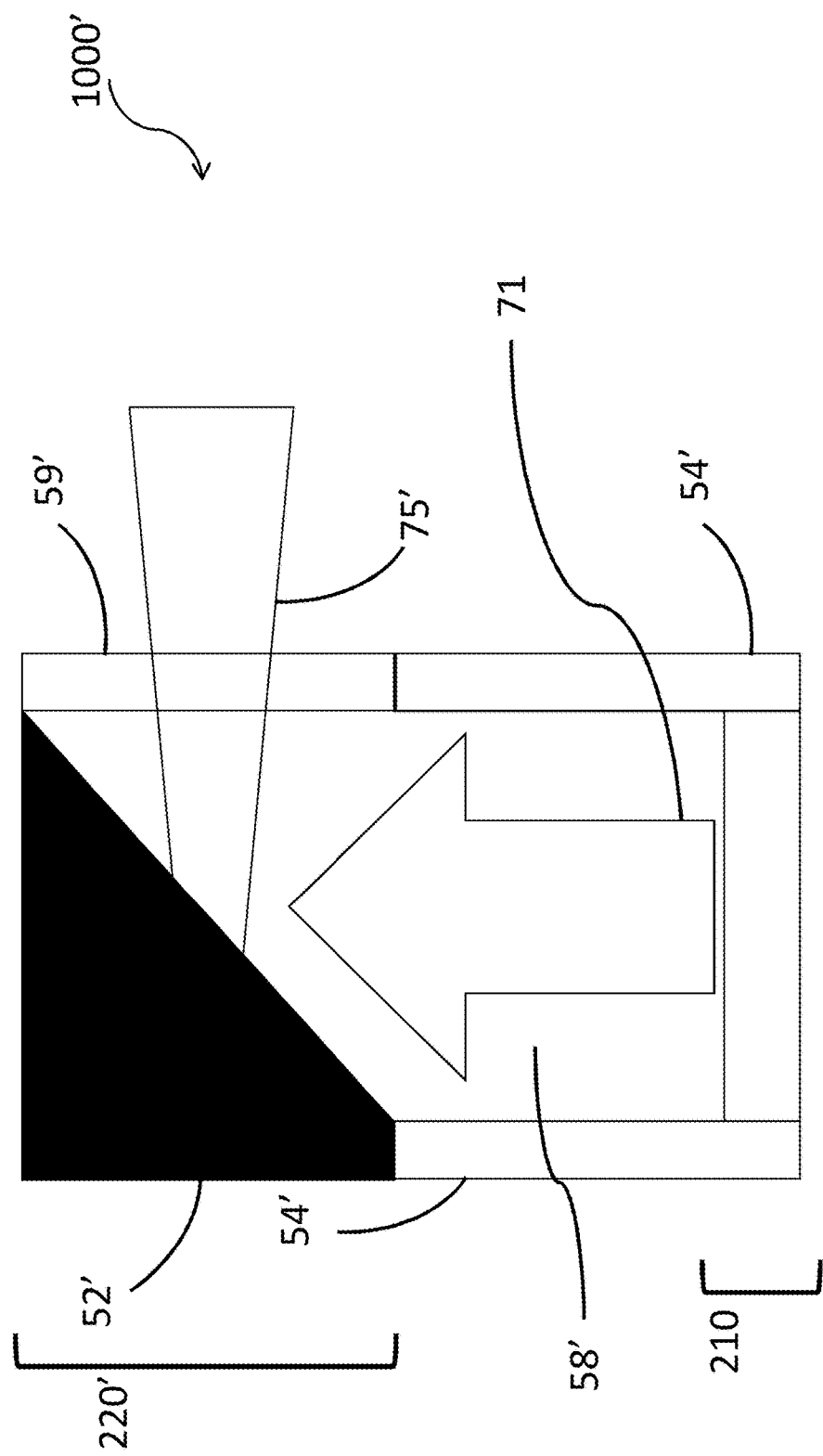
FIG. 7 is a schematic diagram representing a side view of an alternative x-ray emitting device incorporating the electron emitting construct.

The x-rays 75 produced by the anode 52 upon being struck with the electron beam 71 may be transmitted through the anode (as shown in FIG. 6). Alternatively, as shown in FIG. 7, an x-ray emitting device 1000' may be configured such that the electron beam 71 emitted from the electron emitting construct 210 strikes an anode 52' of the x-ray emitting construct 220' that is placed at an angle, say, 45 degrees to the direction of the electron beam 71. In such a configuration, the x-rays 75' created by bremsstrahlung may be emitted at 90 degrees to the incident electron beam 71 and exit the device 1000' sideways through a window 59'.

The x-ray emitting device 1000' includes an electron emitting construct 210' and an x-ray emitting construct 220' facing each other, separated by at least one spacer 54'. The x-ray emitting construct 220' may include an anode 52' and a window 59'. The spacer 54' may be situated such that an inner gap 58' is present between the x-ray emitting construct 220' and the electron emitting construct 210'. The inner gap 58' may be sealed and maintained under vacuum, and may provide an unobstructed space between the electron emitting construct 210' and the x-ray emitting construct 220'.

It will be appreciated that the various options described for the electron emitting construct 210 and its components as described with reference to FIGS. 8-10 hereinbelow are options for the electron emitting constrict 210 incorporated in the x-ray emitting device 1000', the x-ray emitting device 1000', as well as any other device incorporating an electron emitting construct described herein, including image capture devices.

Figure 8:
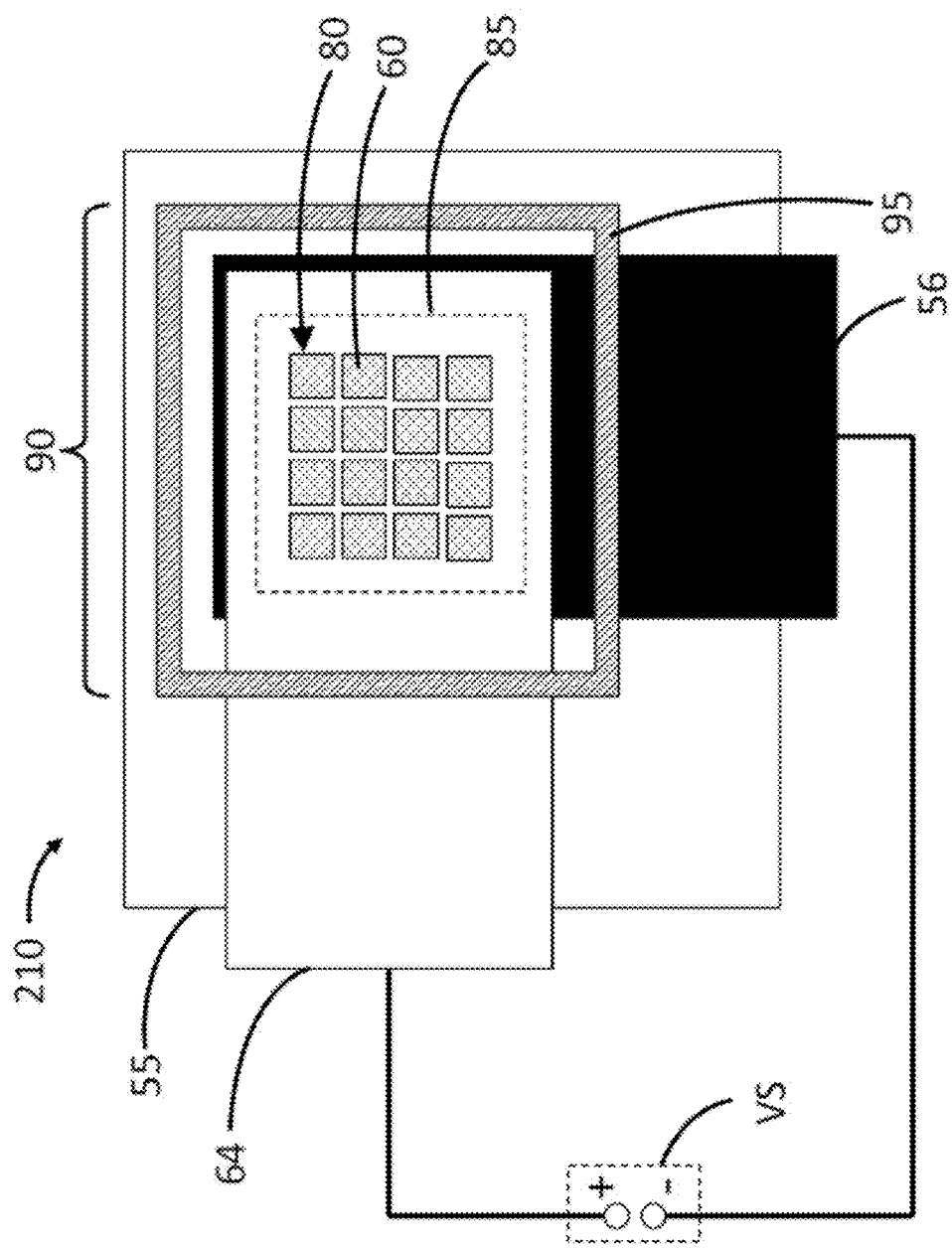
FIG. 8 is a schematic diagram representing an overhead view of an electron emitting construct.

Referring now to FIG. 8, the disclosure provides an electron emission construct 210 including one or more emission units 90. The emission units 90 may be integrated into a substrate 55. The emission unit 90 may include an active zone 85 comprising one or more active areas 80, each active area 80 having a gated cone electron source (not shown) and a gate electrode 60. The gated cone electron source may be a field-emission electron source comprising cones ("emitter tips") arranged in an array, each emitter tip being surrounded by an opening in the gate electrode 60 (a "gate hole"). The active areas 80 are connectable to a voltage source VS through a gate interconnect lead 64, which is conductively connected to the gate electrode(s) 60, as well as through a cathode 56, which overlaps with the gate interconnect lead 64. The emission unit 90 may further include a focus structure 95.

The emission unit 90 is configured to emit an electron beam upon the activation of the gated cone electron source (not shown) incorporated into the one or more active areas 80 present in the active zone 85. The active areas 80 may be activated by connecting the gate interconnect lead 64 (thus also the gate electrode 60) and the cathode 56 to a voltage source VS. The resulting exposure of emitter tips, incorporated into the gated cone electron source, to a voltage gradient causes said emitter tips to emit an electron beam.

Focus Structure

Still with reference to FIG. 8, a field emission type electron source typically emits electrons having a range of trajectories, referred to as the divergence angle, and not all of the electrons are emitted orthogonal to the electron emission construct 210. As such, a mechanism to correct the trajectory of the electrons, while minimizing the loss of electrons emitted at undesirable trajectories, is desired. The focus structure 95 of the disclosure serves that function.

The focus structure 95 may be configured to surround an active zone 85. The focus structure 95 may be configured to suppress scatter of the electron beams emitted from the corresponding active zone 85 through the application of a focus voltage on a focus electrode incorporated therein, thus focusing the emitted electron beam.

In certain embodiments, the focus structure 95 may comprise a first focus structure and a second focus structure, one being situated on top of the other, such that the focus structure 95 comprises, in aggregate, a double focus structure. The second focus electrode may be configured to further accelerate the electrons emitted from the active zone 85 through the application of a second focus voltage, thus further focusing the emitted electron beam. It will be appreciated that the focus structure 95 may comprise, in aggregate, a triple focus structure, a quadruple focus structure, and the like.

The focus structure 95 may further function as a drain for misdirected electrons. In certain embodiments, the focus structure 95 may be positioned to cover a signal line of the driving circuit for the gated cone electron source, thus reducing radiation noise in the signal lines by protecting the signal lines from irradiation by misdirected electrons.

The Gate Electrode

Figure 9A:
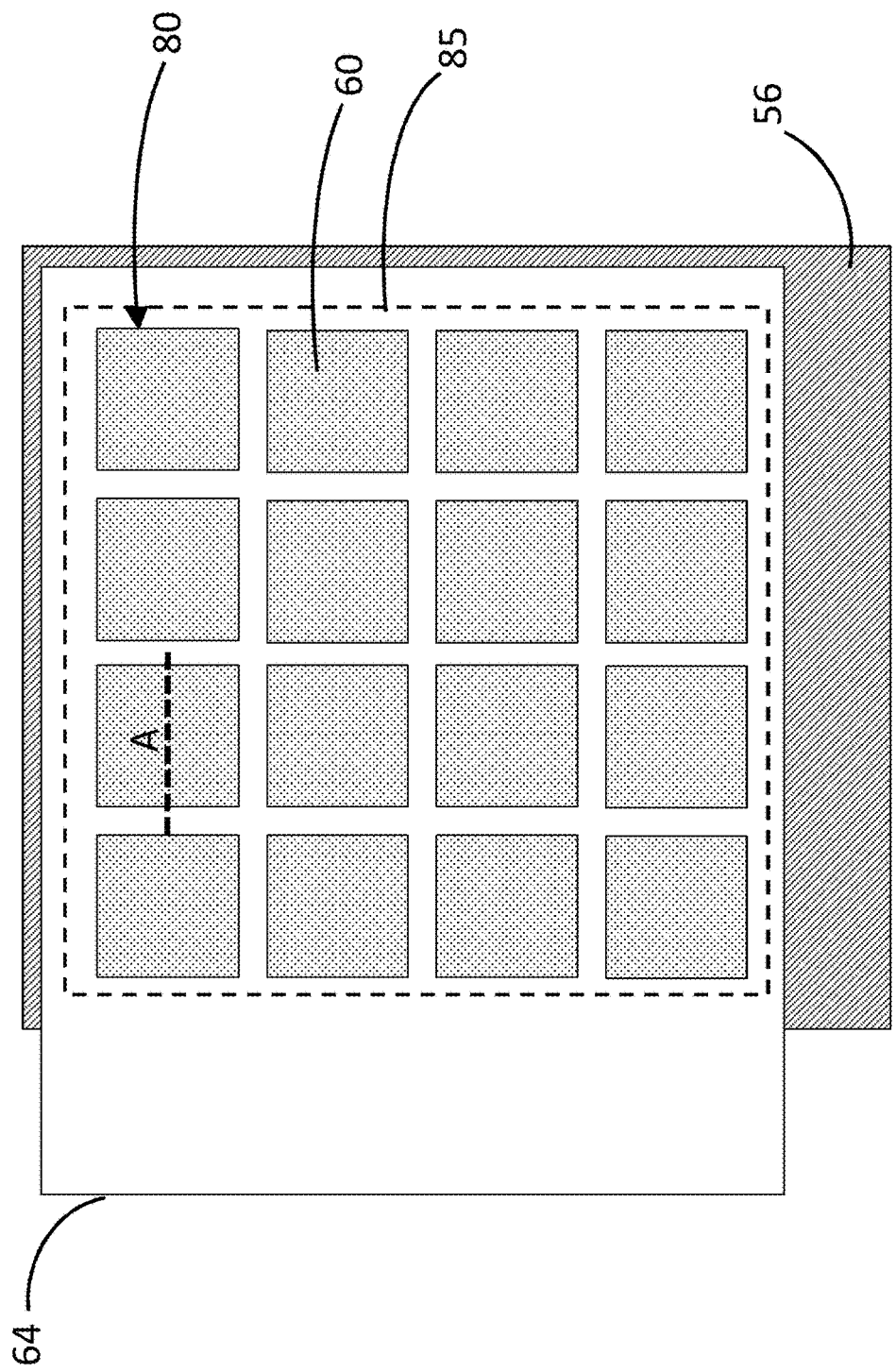

As described above, the active zone 85 is situated at the overlap between the gate interconnect lead 64 and the cathode 56. As shown in FIG. 9A, each active area 80 may be situated in a fully enclosed gap within the gate interconnect lead 64. That is, each active area 80 may be an island surrounded by the gate interconnect lead 64. As such, the gate electrode 60 may be conductively connected to the gate interconnect lead 64 from any or all lateral sides.

As shown in FIG. 9A, the active zone 85 includes sixteen active areas 80. However it will be appreciated that the active zone 85 may have as many active areas as deemed appropriate for the use of the electron emitting construct 210. Variously, there may be as few as one active area 80, as many as a hundred (e.g., 10×10 active areas 80), as many as a thousand (e.g., 100×100 active areas 80), or more active areas 80, in the active zone 85.

While the active areas 80 shown in FIG. 9A are square in shape, the active area 80 may be, variously, rectangular, circular, bent bands, pie-shapes or the like. Similarly, the active area 80 may be, variously, rectangular, circular, bent bands, pie-shapes or the like. In addition, multiple active areas 80 may be arranged in the active zone 85 in a square grid pattern (as shown in FIG. 9A), a rectangular grip pattern, a radial pattern, or the like.

The active area 80 may be in a square shape, for example, of about 2 mm×2 mm, about 1.5 mm×about 1.5 mm, about 1.0 mm×1.0 mm, about 750 microns×750 microns, about 500 microns×500 microns, about 400 microns×400 microns, about 300 microns×300 microns, about 200 microns×200 microns, about 150 microns×150 microns, about 100 microns×100 microns, about 75 microns×75 microns, about 50 microns×50 microns, about 25 microns×25 microns, about 10 microns×10 microns, or between 75 microns and 125 microns. An active area 80 having dimensions about 2 mm×2 mm has a size (i.e., surface area) of about 4 square millimeters (mm$^2$), an active area 80 having dimensions of about 10 microns×10 microns has a size of about 100 square microns, and so forth.

The size of the active zone 85 depends on the size of the active area 80 and the number of active areas 80 within the active zone 85, as well as the width of the portion of the gate interconnect lead 64 interspersed between, and surrounding, each active area. Typically, the dimensions of the active zone 85 may be about 10-20% greater than the aggregate dimensions of the active areas 80 along the same side, due to the interspersed portions of the gate interconnect lead 64. For example, in an active zone 85 having sixteen active areas 80 arranged in a four-by-four grid, each active area 80 having a size of 100 microns by 100 microns, each active area 80 being interspersed by a portion of the grid interconnect lead 64, the active zone 85 may have a size of about 480 microns by 480 microns (in a case where the interspersed portions of the gate interconnect lead 64 adds 20% to the width of the active zone).

The emission unit may be configured such that all active areas 80 of the active zone 85 are configured to be co-activated. Alternatively, each active area 80 (or different subsets of active areas 80) within an active zone 85 may be capable of being activated independently, that is, an individual active area 80, or a subset of the active areas 80, may be activated while the remaining active areas 80 within the active zone 85 remain inactive. Thus, the active areas 80 may be activated in various spatial and temporal patterns. As such, subsets of active areas 80 may be activated to realize different emission currents for the active zone 85. Alternatively or in addition, subsets of active areas 80 encompassing different concentric regions of the active zone 85 may be activated separately to realize different sizes of the initial width, e.g., the cross-sectional area, of the emitted electron beam by the active zone 85, and, thus, the focal spot size of the emitted electron beam. In other words, the emission current of the electron beam emitted by the active zone 85 may be capable of being tuned through the controlled activation of one or more of the active areas 80 within the active zone 85, and the initial width of the electron beam emitted by the active zone 85 may be capable of being tuned through the controlled activation of one or more subsets of the active areas 80 organized as concentric regions.

As a particular embodiment, an active zone having nine active areas arranged in a 3×3 grid may be divided into two concentric regions, the first concentric region encompassing the central active area and the second concentric region encompassing the outer eight active areas. As an alternative embodiment, an active zone having twenty-five active areas arranged in a 5×5 grid may be divided into three concentric regions, the first concentric region encompassing the central active area, the second concentric regions encompassing the eight intermediate active areas, and the third concentric region encompassing the sixteen outer active areas. It will be appreciated that an active zone may be configured to have a yet larger array of active areas, having, e.g., four, five, six or more concentric regions.

Figure 9B:
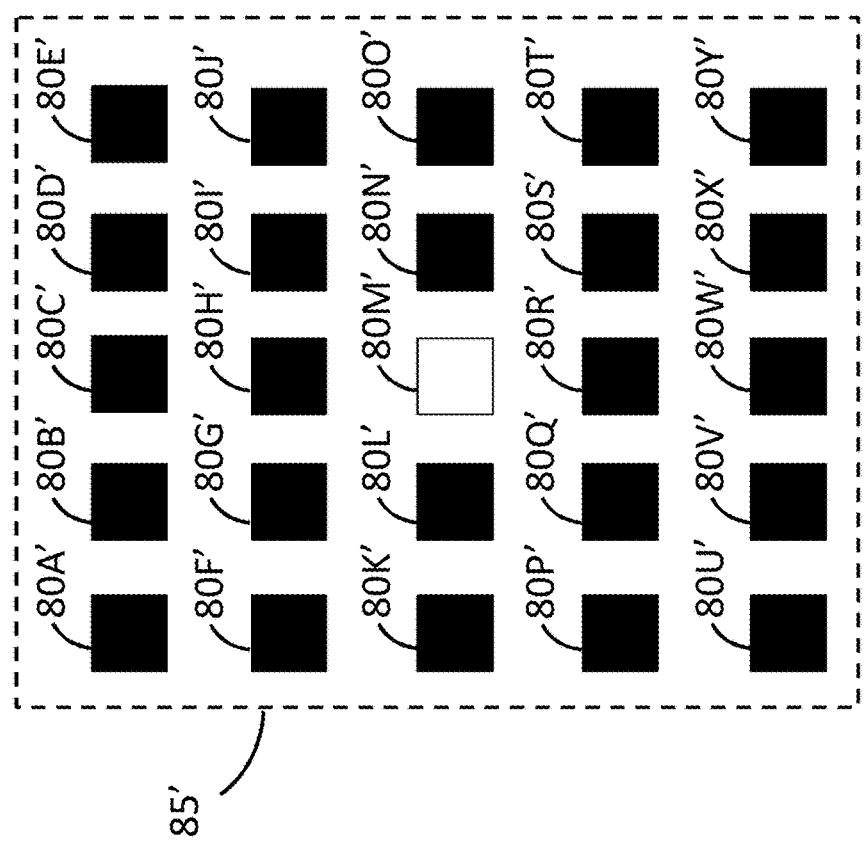
Figure 9D:
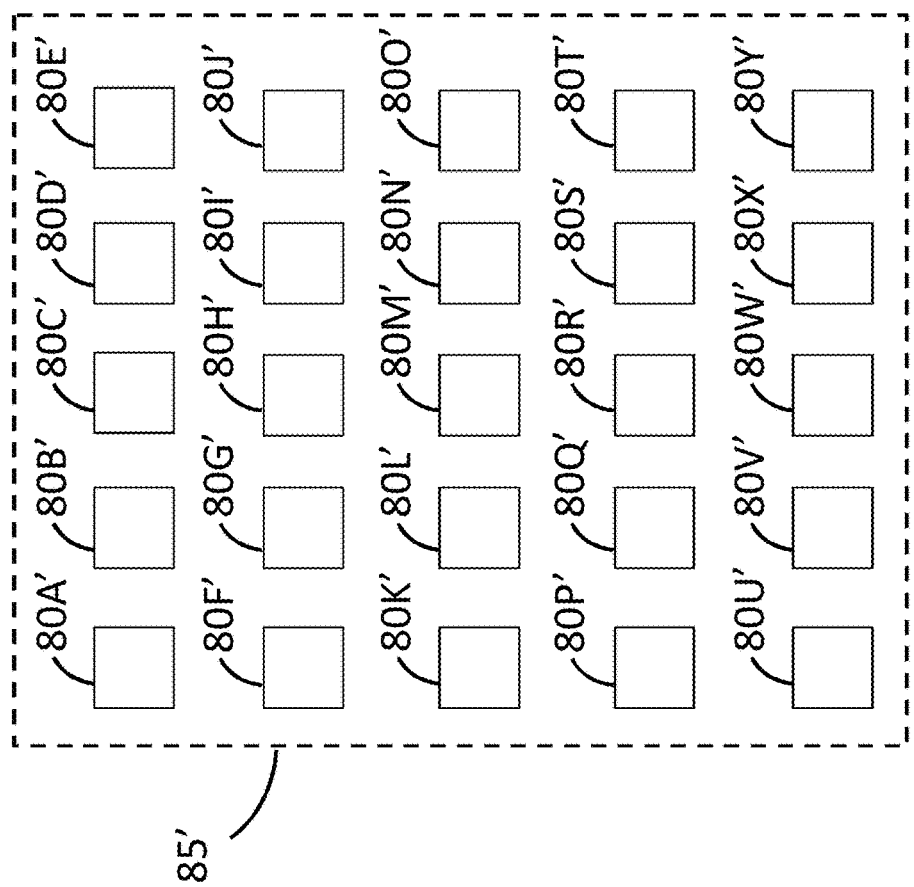

Referring now to FIGS. 9B-D, showing an active zone 85' having twenty-five active areas 80A'-80Y' arranged in a 5×5 grid pattern, said active zone 85' may have three concentric regions that are separately activatable: a first region including the center active area 80M'; a second concentric region including the intermediate active areas 80G', 80H', 80I', 80L', 80N', 80Q', 80R' and 80S'; and a third concentric region including the outer active areas 80A'-80E', 80F', 80J', 80K', 80O', 80P', 80T' and 80U'-80Y'. As shown in FIG. 9B, activating the first concentric region (the activated active areas 80' being shown in white) while keeping the second and third concentric regions inactive (the inactive active areas 80' being shown in black) will result in the emission of a narrow electron beam with a small emission current (FIG. 9B). Alternatively, activating the first and second concentric regions together, while keeping the third concentric region inactive will result in the emission of an electron beam of intermediate width with an intermediate emission current (FIG. 9C). Finally, activating all three concentric regions, i.e., all twenty-five active areas, will result in the emission of a wide electron beam with a large emission current (FIG. 9D).

It will be appreciated that the above disclosure, in relation to FIGS. 9A-D, provides for methods of tuning the emission current and/or the initial width of an electron beam emitted by an active zone comprising multiple active areas. It will further be appreciated that said methods may be applied to active areas having any type of electron source, and are not limited active areas having a gated cone electron source. As such, the above-described methods may be applied to, for example, a Spindt type electron source, a carbon nanotube (CNT) type electron source, a metal-insulator-metal (MIM) type electron source or a metal-insulator-semiconductor (MIS) type electron source.

Further Features of the Electron Emitting Construct

Figure 10:
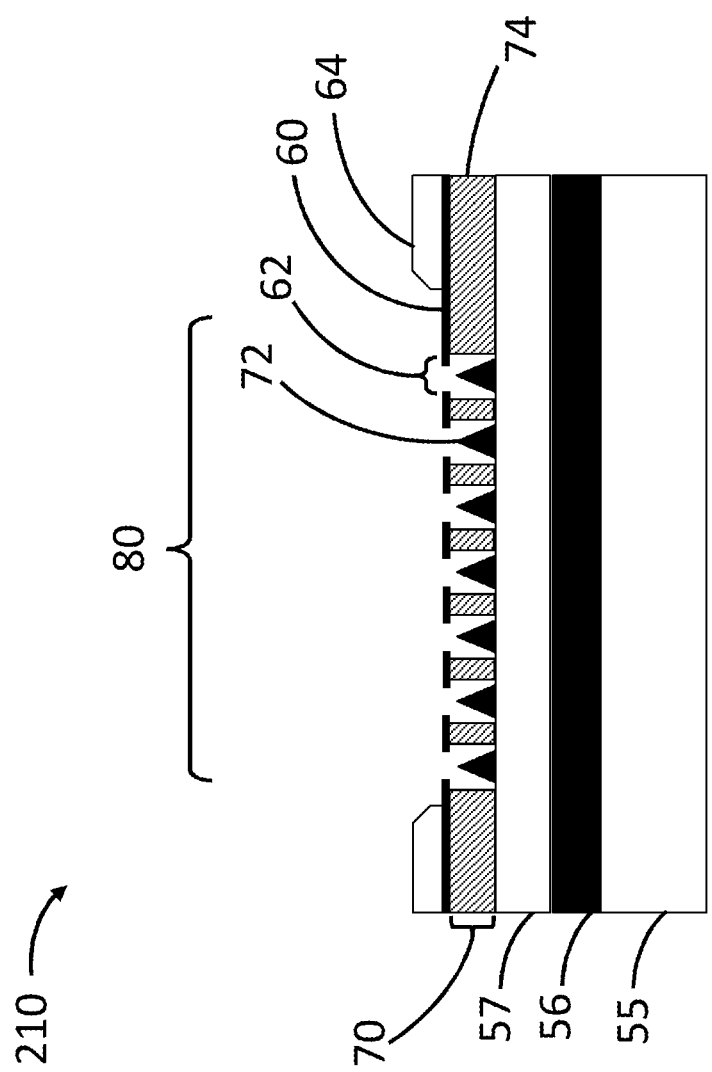
FIG. 10 is schematic diagram representing a side view (along, e.g., line A of FIG. 9A) of an active area of the electron emitting construct.

With reference to FIG. 10, an active area 80 of the electron emitting construct 210 may comprise a substrate 55, a cathode 56, a resistive layer 57, a gated cone electron source 70, and a gate electrode 60. As discussed above, the active area 80 may be defined as the area occupied by the gated cone electron source 70 and/or the corresponding gate electrode 60. The active area 80 may also be defined as the area enclosed by the gate interconnect lead 64.

The gated cone electron source 70 may comprise a plurality of emitter tips 72 arranged in an array. The gated cone electron source 70 may further comprise an interlevel dielectric (ILD) layer 74 having a plurality of ILD windows, with an emitter tip 72 being situated at each ILD window. The ILD 74 may further serve as a support for the gate electrode 60 situated thereupon.

The emitter tip 72 may be constructed of, e.g., chromium, molybdenum or the like. Each emitter tip 72 may be about 500 nanometers (nm), about 400 nm, about 300 nm, about 200 nm, about 100 nm, less than 500 nm, less than 400 nm, less than 300 nm, less than 200 nm, less than 100 nm, between 100 and 300 nm, or between 200 and 400 nm in height. Each emitter tip may be about 500 nm, about 400 nm, about 300 nm, about 200 nm, about 100 nm, less than 500 nm, less than 400 nm, less than 300 nm, less than 200 nm, less than 100 nm, between 100 and 300 nm, or between 200 and 400 nm in width at the base. In a particular embodiment, the emitter tip 72 may be less than 300 nm in height and less than 300 nm in width at the base.

The gate electrode 60 may comprise a plurality of gate holes 62. The gate electrode 60 may be constructed out of a conductive material such as chromium, niobium or the like. Typically, the position of the gate holes 62 corresponds to the position of the ILD windows and the emitter tips 72, such that each emitter tip is configured to emit an electron beam outwards out of the gate hole 62. The gate hole 62 may have a diameter of between 50 and 500 nanometers, between 100 and 400 nanometers, between 150 and 250 nanometers, about 100 nanometers, about 150 nanometers, about 175 nanometers, about 200 nanometers, about 225 nanometers, about 250 nanometers, about 300 nanometers, about 350 nanometers, less than 300 nanometers, less than 250 nanometers, less than 200 nanometers, less than 150 nanometers, and less than 100 nanometers.

The gate electrode 60 may be conductively connected to a voltage source via the gate interconnect lead 64. The gate electrode 60 may have a thickness of about 50 nanometers (nm), about 60 nm, about 70 nm, about 80 nm, about 90 nm, about 100 nm, about 125, between 50 nm and 125 nm or between 80 nm and 100 nm. The gate interconnect lead 64 may have a thickness of between 0.5 microns and 20 microns. As such, the gate electrode 60 is thinner than the gate interconnect lead 64. Due to the thinness, as well as the presence of the gate holes 62, the resistance of the gate electrode 60 is substantially higher than the resistance of the gate interconnect lead 64.

The resistive layer 57 is situated between the cathode 57 and the gated cone electron source 70, and serves to regulate the electric current that flows between the cathode 57 and the emitter tips 72 during their activation, among other functions. The resistive layer 57 may comprise silicon carbon nitride (SiCN), silicon carbide or amorphous silicon. The resistive layer 57 may further comprise a barrier sublayer at one or more of its exterior surface. That is, the resistive layer 57 may comprise a barrier sublayer situated at the interface with the cathode, at the interface with the gated cone electron source, or situated at both the cathode interface and the gated cone electron source interface. The barrier sublayer may comprise a carbon-rich SiCN layer or a nitrogen-rich SiCN layer.

SiCN encompasses a wide range of compositions. SiCN may be represented by $Si(x)C(y)N(z)$, where x, y, z shows the atomic percentage of each element. For example, $Si(x)C(y)N(z)$ composed of x=75%, y=15% and z=10%, refers to a silicon carbon nitride composition where 75% of the atoms are silicon, 15% of the atoms are carbon and 10% of the atoms are nitrogen. This notation of SiCN includes cases where the atomic percentage is 0. For example, Si(x)C(y)N(z) with the composition of z=0%, is silicon carbide (SiC). Similarly, if x=0% and z=0% then y=100%, which is pure carbon, e.g., amorphous carbon.

A typical resistive layer 57 may utilize Si(x)C(y)N(z) composed of, for example, x=47%, y=47%, z=6%. A nitride-rich or carbon-rich barrier layer may be SiCN with a higher y value (carbon atomic percentage) or a higher z value (nitrogen atomic percentage) in comparison to the Si(x)C(y)N(z) utilized in the resistive layer 57. For example, the nitride-rich or carbon-rich barrier layer may be SiCN or SiC having a silicon atomic percentage of less than 40%. As a further example, if the above Si(x)C(y)N(z) composed of x=47%, y=47%, z=6%, utilized in the resistive layer 57, a nitrogen rich barrier layer may utilize Si(x)C(y)N(z) composed of x=30%, y=30%, z=40%, and a carbon rich barrier layer may utilize Si(x)C(y)N(z) composed of x=30%, y=65%, N=5%. Alternatively, the carbon-rich barrier layer may be amorphous carbon. The x, y and z values for Si(x)C(y)N(z) compositions can be controlled by various methods known in the art, e.g., deposition conditions using sputter of chemical vapor deposition (CVD).

The cathode 56 may comprise copper (Cu) or aluminum (Al), and may be of a thickness of between 0.5 microns and 20 microns.

It will be appreciated that in the electron emitting construct 210 of the present disclosure, the gated cone electron source 70, the resistive layer 57 and the cathode 56 are vertically aligned. That is, the gate electrode 60, gated cone electron source 70, the resistive layer 57 and the cathode 56 all overlap each other along the plane of active area 80 and the electron emitting construct 210. Further, the position of each of the emitter tips 72, the corresponding gate hole 62, the cathode 56 and the resistive layer 57 may overlap along the plane of the electron emitting construct. Such an arrangement presents little or no lateral displacement between each of the above components, and results in (among other effects): maintaining the uniformity of the voltage gradient between the gate electrode 60 and the cathode 56; and maintaining the uniformity of the path of, and the resistances encountered by, the electrical current provided to each individual emitter tip 72.

The substrate 55 may comprise a semiconductor material, for example, crystallized silicon. Further, any one of the cathode 56, the resistive layer 57, the gated cone electron source 70 including the emitter tip 72 and the ILD 74, the gate electrode 60, the lead interconnect lead 64 or any combination thereof, may be processed on, and integral to, the substrate 55.

X-Ray Imaging System

The present disclosure further provides for an X-ray imaging system comprising at least one x-ray emitting device as described herein and at least one image capture device as described herein, situated such that the x-ray emitting device emits an x-ray beam towards the electron receiving construct of the image capture device, which may include a photoconductor.

Figure 11A:
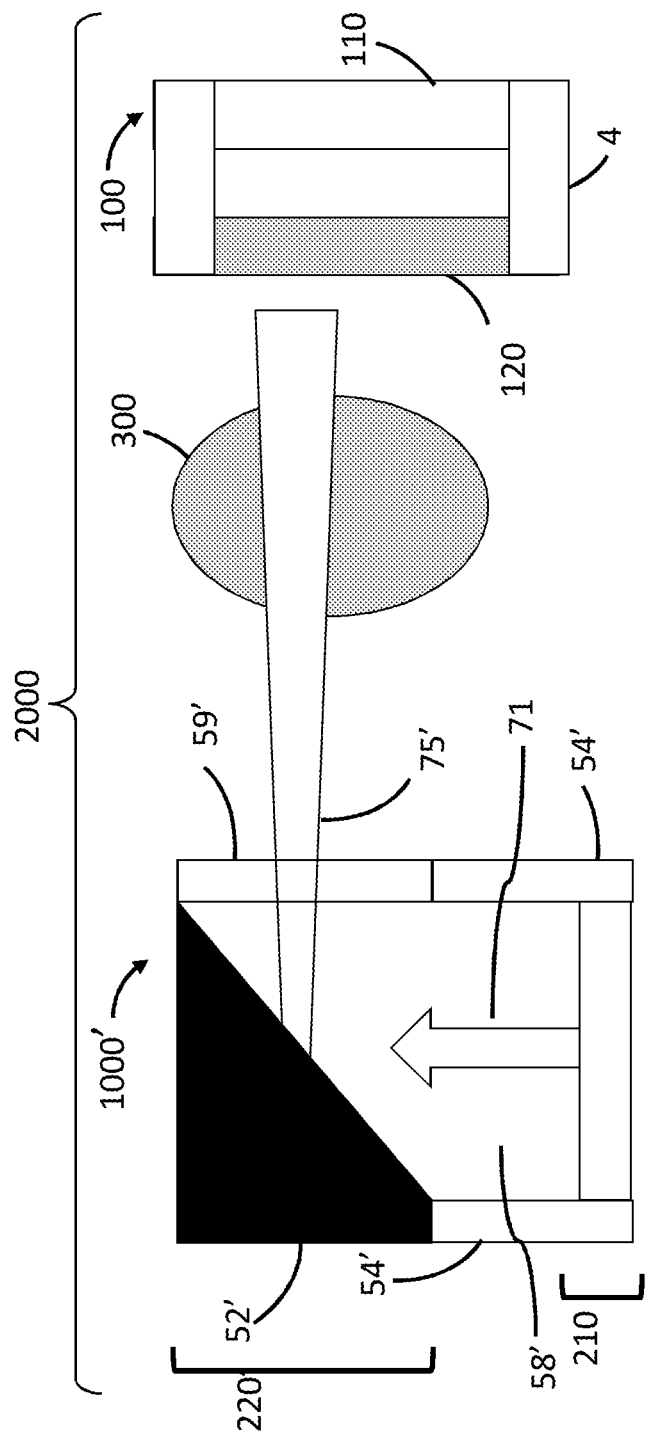
FIGS. 11A-D are schematic diagrams of an x-ray imaging system according to the present disclosure.

FIG. 11A shows an x-ray imaging system 2000, comprising an image capture device 100 and an x-ray emitting device 1000'.

The image capture device 100 includes an electron emitting construct 110 and an electron receiving construct 120, separated by a spacer 4. The spacer 4 may be situated such that an inner gap 30 is present between the electron receiving construct 120 and the electron emitting construct 110. The inner gap 30 may be sealed and maintained under vacuum, and may provide an unobstructed space between the electron emitting construct 110 and the electron receiving construct 120. The electron receiving construct 110 may comprise a photoconductor, and be configured to receive x-rays emitted by the x-ray emitting device 1000'. The image capture device 100 and its components are described in further detail elsewhere herein.

The x-ray emitting device 1000' may be configured such that the electron beam 71 emitted from the electron emitting construct 210 strikes an anode 52' of the x-ray emitting construct 220' that is placed at an angle, say, 45 degrees to the direction of the electron beam 71. In such a configuration, the x-rays 75' created by bremsstrahlung may be emitted at 90 degrees to the incident electron beam 71 and exit the device 1000' sideways through a window 59'. The x-ray emitting device 1000' and its components are described in further detail elsewhere herein.

The x-ray imaging system 2000 is configured to allow an object 300 to be placed between the x-ray emitting device 1000' and the image capture device 100, such that the x-rays 75' (or a portion thereof) traverse the object 300 (or a portion thereof) before striking the image capture device 100 (or a portion thereof), thereby producing an x-ray transmission image of the object 300.

Figure 11B:
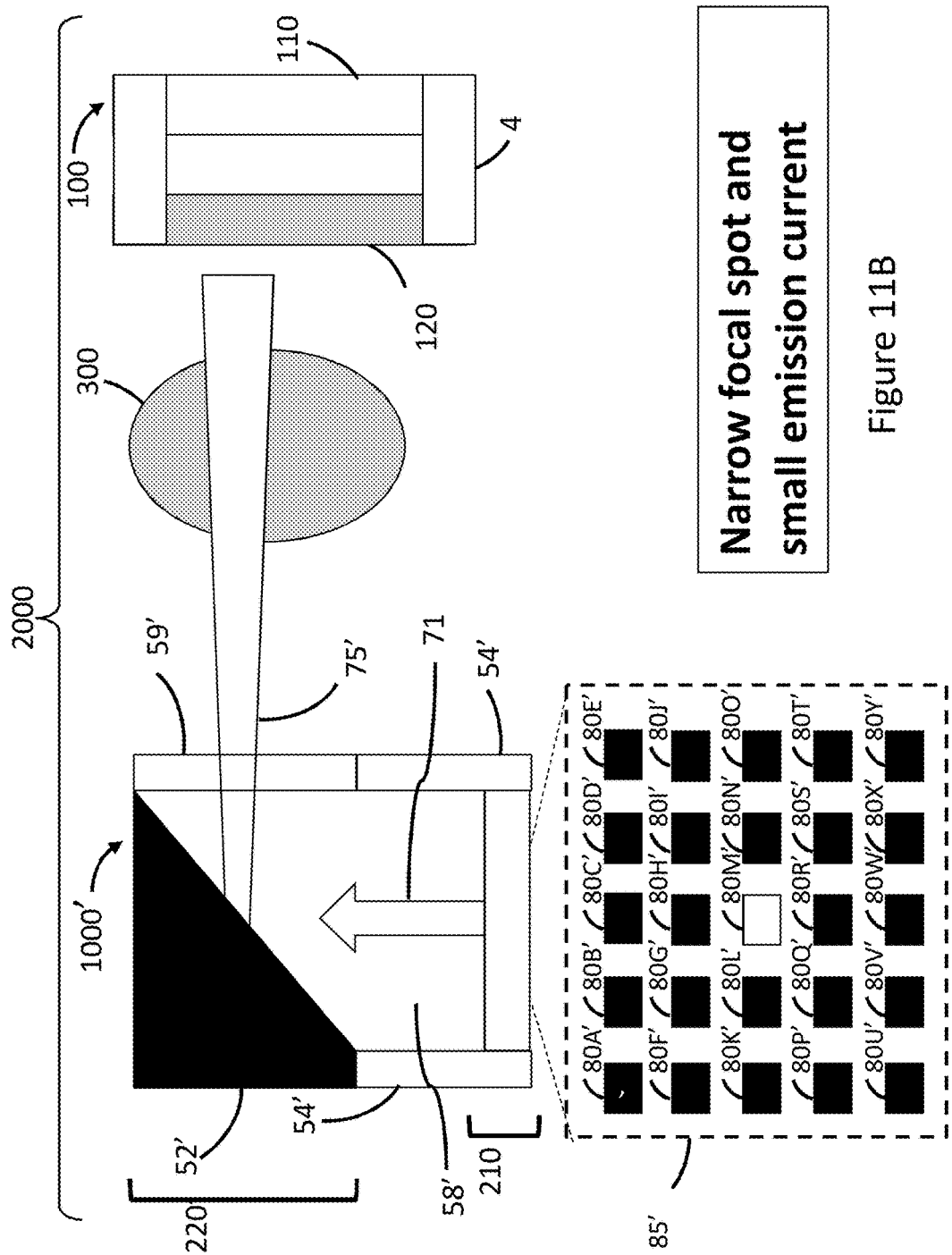
Figure 11C:
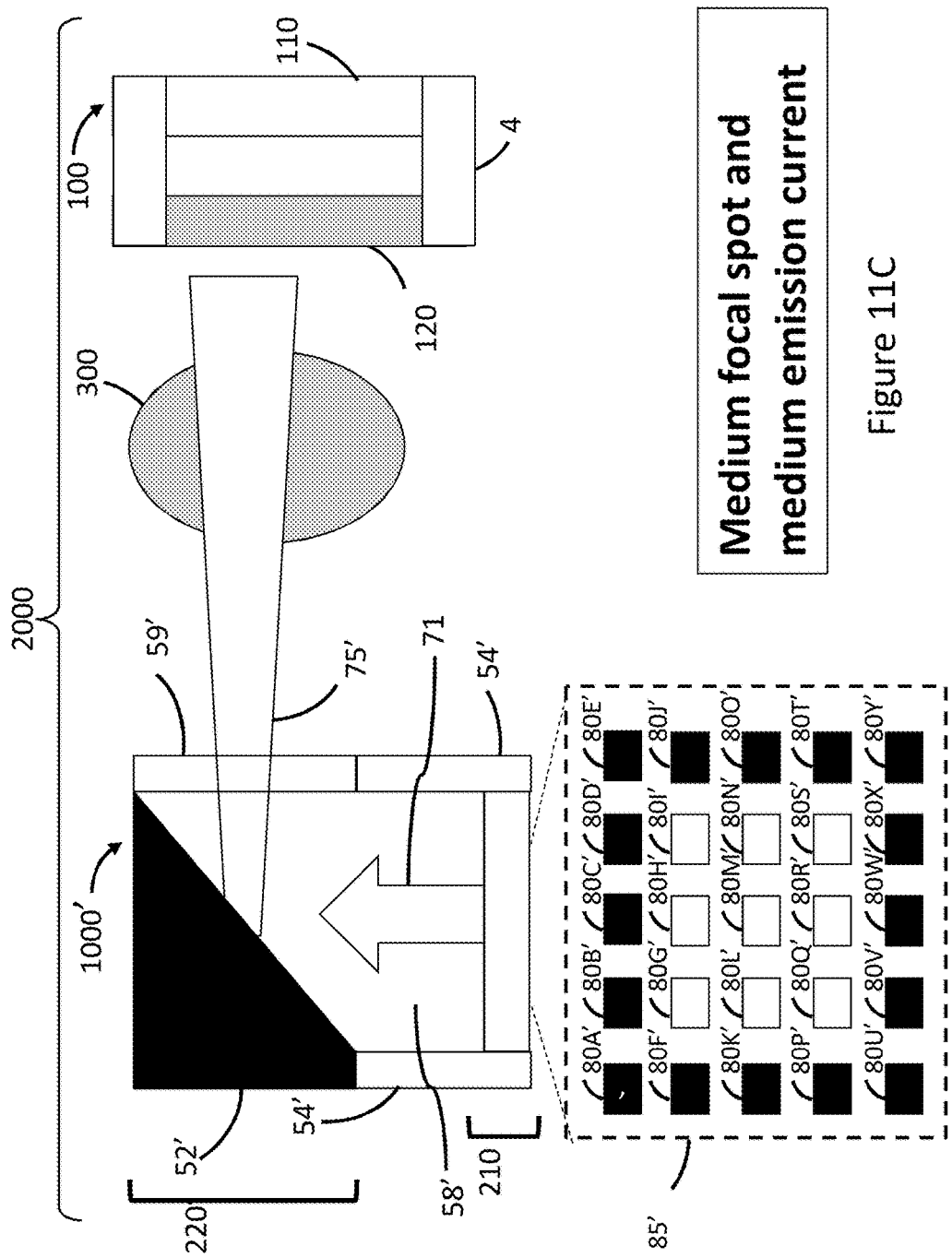
Figure 11D:
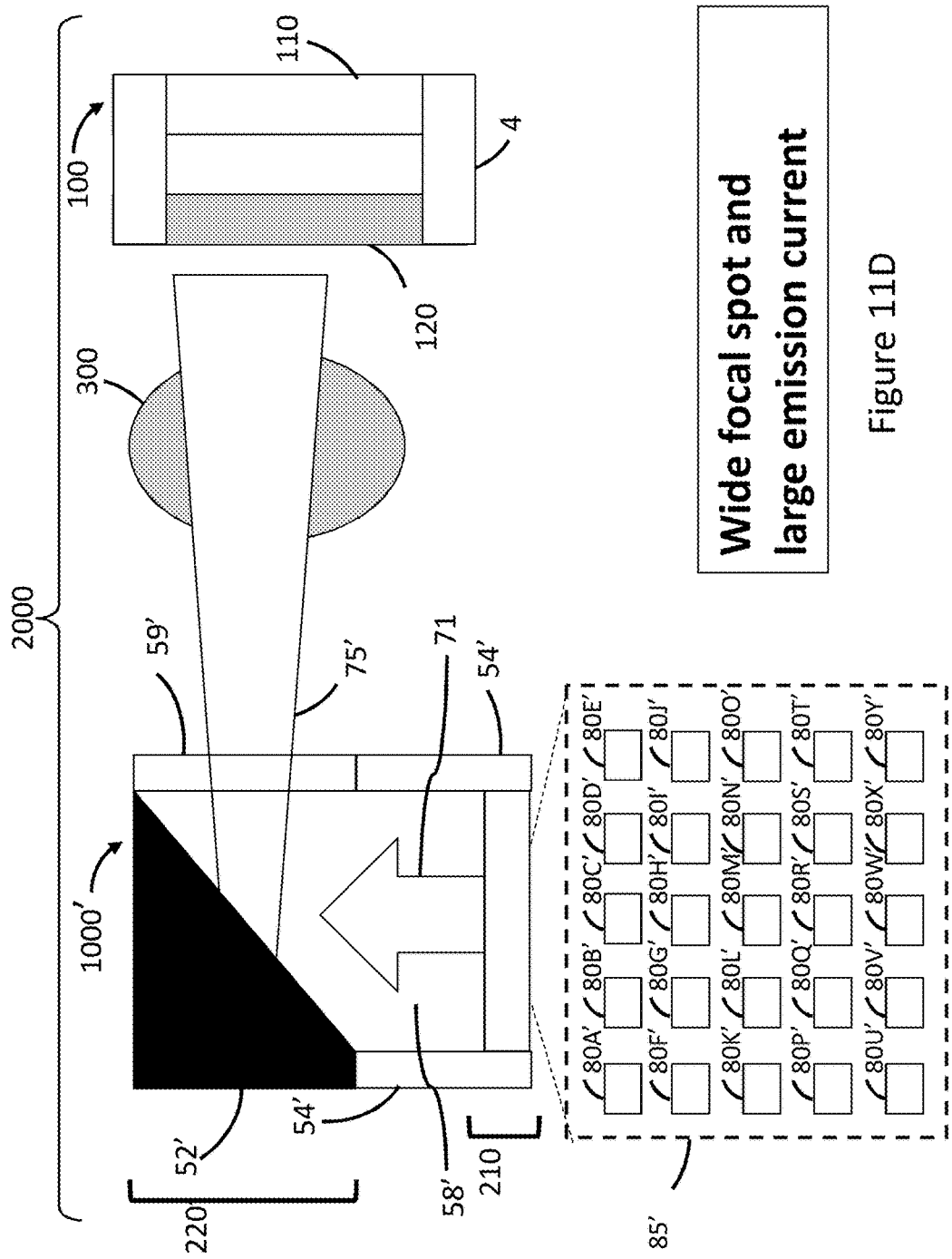

The power and/or width of the x-ray emitting by the x-ray emitting device 1000' in the x-ray imaging system 2000 may be tunable. Reference is now made to FIGS. 11B-D, showing the x-ray imaging system 2000 with an expanded view of an active zone 85' incorporated into the electron emitting construct 210, having twenty-five active areas 80A'-80Y' arranged in a 5×5 grid pattern. The active zone 85' may have, for example, three concentric regions that are separately activatable: a first region including the center active area 80M'; a second concentric region including the intermediate active areas 80G', 80H', 80I', 80L', 80N', 80Q', 80R' and 80S'; and a third concentric region including the outer active areas 80A'-80E', 80F', 80J', 80K', 80O', 80P', 80T' and 80U'-80Y'.

As shown in FIG. 11B, activating the first concentric region (the activated active areas 80' being shown in white) while keeping the second and third concentric regions inactive (the inactive active areas 80' being shown in black) will result in the emission of a narrow electron beam with a small emission current, such that the x-ray emitting device 1000' emits a narrow x-ray beam (FIG. 11B). Alternatively, activating the first and second concentric regions together, while keeping the third concentric region inactive will result in the emission of an electron beam of intermediate width with an intermediate emission current, such that the x-ray emitting device 1000' emits an x-ray beam of intermediate width (FIG. 11C). Finally, activating all three concentric regions, i.e., all twenty-five active areas, will result in the emission of a wide electron beam with a large emission current, such that the x-ray emitting device 1000' emits a wide x-ray beam (FIG. 11D).

It will be appreciated that an x-ray imaging system, as provided in the present disclosure, may comprise any x-ray emitting device as described herein, for example, as shown in and described in reference to FIGS. 6-10, and may comprise any image capture device as described herein, for example, as shown in and described in reference to FIGS. 2-5. It will be further appreciated that an x-ray imaging system, as provided in the present disclosure, may comprise multiple x-ray emitting devices and/or multiple image capture devices.

Functional Features of the Electron Emitting Construct

As described above (with respect to FIGS. 8, 9A-D and 10), the active area 80 and the corresponding gate electrode 60 may be surrounded by portions of the gate interconnect lead 64. That is, the gate electrode 60 of an active area 80 may be situated in a fully enclosed gap within the gate interconnect lead 64. Compared to the active zone 85 having one large active area 80, the above-described arrangement of having multiple active areas 80 has various advantages, for example reducing the path length of an electric current through the high-resistance gate electrode 60 which may improve the uniformity of the voltage gradient between the gate electrode 60 and the cathode 56 along the plane of the gated cone electron source 70. Furthermore, this arrangement has the added effect of evening out the temperature distribution of the active zone 85, as the gate interconnect lead 64 may be a better heat conductor than the gate electrode 60.

Due to the small (sub-micron) size of the emitter tips 72 and the gate holes 62, the gated cone electron source 70 may be considered to be a nano gated cone electron source. It is particularly noted that the small size of the individual elements of the gated cone electron source 70, e.g., the emitter tips 72, in combination with the small diameter of the gate holes 62, allows for the placement of a large number of emitter tips 72 in each active area 80 and thus in each active zone 85. For example, the active area 80 may include about 1 emitter tip 72 per square micron. That is, in an active area 80 of 10,000 square microns (100 microns×100 microns) the small size of the emitter tips 72 and the gate holes 62 may allow for the placement of about 10,000 emitter tips 72. Based on the base width of the emitter tips 72 and other features of the gated cone electron source 70, as well as features of the gate electrode 60, the gated cone electron source 70 may have an emitter tip density that is higher than one emitter tip 72 per square micron, e.g., between one and ten emitter tips 72 per square micron, between two and four emitter tips per square micron, or the like. Thus, the small size of the emitter tips 72 and gate holes 62 enables a high density of emitter tips 72 to produce high flux density through the gated cone electron source 70 while allowing the current passing through each emitter tip 72 to be low, thus also resulting in improved lifespan, stability and uniformity in the function of the gated cone electron source.

The gated cone electron source 70 may be capable of passing an electrical current having a flux density (i.e., may be capable of having an emission current density) of between 1 and 10 mA/mm$^2$ (milliAmperes per square millimeter).

The gated cone electron source 70 may be configured to emit an electron beam with an initial velocity of about 5 eV, about 10 eV, about 15 eV, about 20 eV or between 5 and 15 eV.

It will be appreciated that, given a certain emission current density that the gated cone electron source 70 is capable of passing (as described above), the emission current of an active area 80 will depend on its size (e.g. the surface area). Similarly, the emission current of an active zone 85 will depend on the number of active areas 80 it contains. For example, an active area 80 of 100 microns×100 microns in size, having an emission current density of 10 mA/mm$^2$, has an emission current of 0.1 mA. As such, an active zone that is 1.1 mm$^2$ in size, having 100 such active areas 80, has an emission current of 10 mA. Similarly, an active zone that is 11 mm$^2$ in size, having 1000 such active areas 80, has an emission current of 100 mA. Also similarly, an active zone that is 55 mm$^2$ in size, having 5000 such active areas 80, has an emission current of 500 mA. Therefore, the emission current of the active zone 85 may be as low as 10 mA, or as much as 500 mA, or higher.

The cathode 56 may be configured to pass a current (a "cathode current") of about 10 mA, about 50 mA, about 100 mA, about 200 mA, about 300 mA, about 400 mA, about 500 mA, about 600 mA, about 700 mA, about 800 mA, about 900 mA, about 1 A, more than 800 mA, between 500 and 700 mA, between 300 mA and 800 mA, between 100 mA and 800 mA, between 10 mA and 1 A, at least 500 mA at least 600 mA, at least 700 mA or at least 800 mA. The cathode current may comprise the emission current of the corresponding active zone 85 (as described above) and a gate leakage current through the corresponding gate electrodes 60 (and the corresponding gate interconnect lead 64). Typically, the gate leakage current is small in comparison to the emission current, and as such, the cathode current is similar to, or slightly higher than, the emission current of the active zone 85.

Application of the X-Ray Emitting Device

The x-ray emitting device provided in the present application may be arranged in various geometries to satisfy a range of x-ray system configurations, including CT scanners, cone beam CT, electron beam CT, other tomographic modalities including breast tomosynthesis tomography, reverse geometry x-ray configurations (in which an extended x-ray source which can emit x-rays from various positions quickly is placed close to the patient, and the x-ray detector is placed far from the patient) and other configurations which require rapid switching between stationary x-ray sources placed in various locations around the patient.

EXAMPLES

Example 1

Simulation of the Effect of Focus Structures

Figure 12:
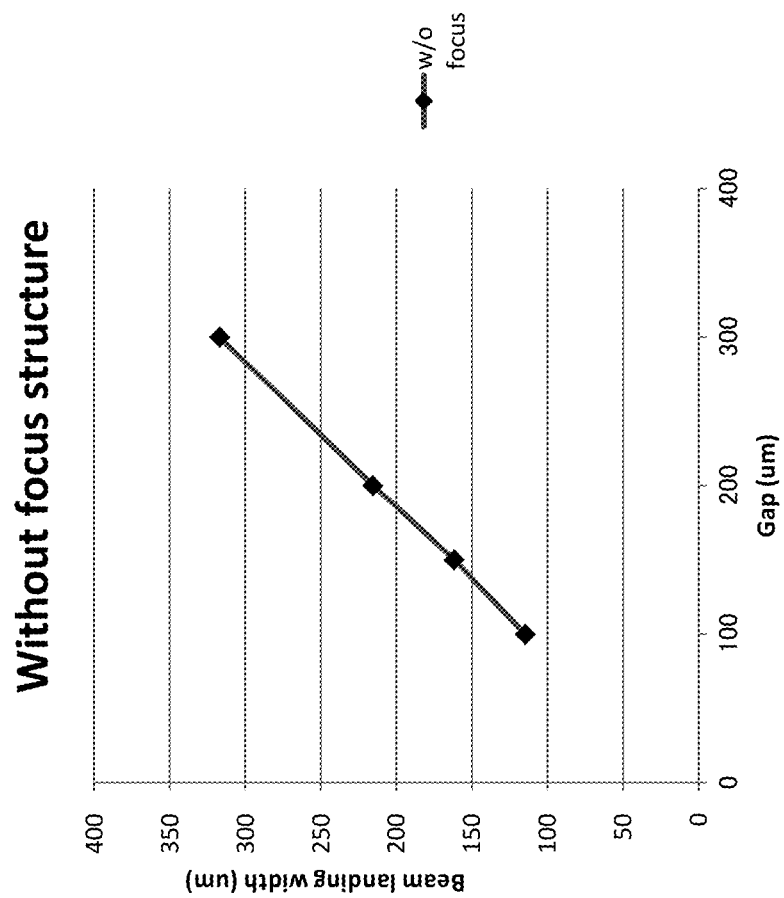
FIG. 12 shows the results of a simulation showing the effect of the width of the distance between the electron emitting construct and the electron receiving construct (Gap) on the width of the area on the photoconductor that is struck by the electron beam from the electron sources of an emitter area (beam landing width).

FIG. 12 shows the results from a simulated image capture device depicting how the width of an electron beam at the point where it strikes the opposing surface of an electron receiving construct facing it (e.g., a photoconductor in the case of an image capture device of the disclosure or an x-ray target in the case of an x-ray emitting device of the disclosure), increases as the gap between the electron emitting construct and the electron receiving construct increases. With reference to FIG. 12 (as well as FIGS. 13-15), the beam landing width, or the focal spot size, refers to the width of an electron beam at the point where it strikes the electron receiving construct facing it, and the gap refers to the distance between the anode (on the electron receiving construct) and the cathode (on the electron emitting construct).

In many cases, it is desirable that the beam landing width remain narrow. For example, in the case of in the case of an image capture device, it is desirable that the focal spot size is not more than the pixel pitch, so that the electron beam emitted from one emitter area does not overlap with the electron beam emitted from an adjacent emitter area. Given the widening of the beam landing width with gap distance, the pixel pitch that can be achieved within a certain gap distance is limited. The focus structures/electrodes serve to restrict the widening of the beam landing width with gap distance, thus e.g., enabling smaller pixel pitch with a larger gap (e.g., between anode and cathode).

Figure 13:
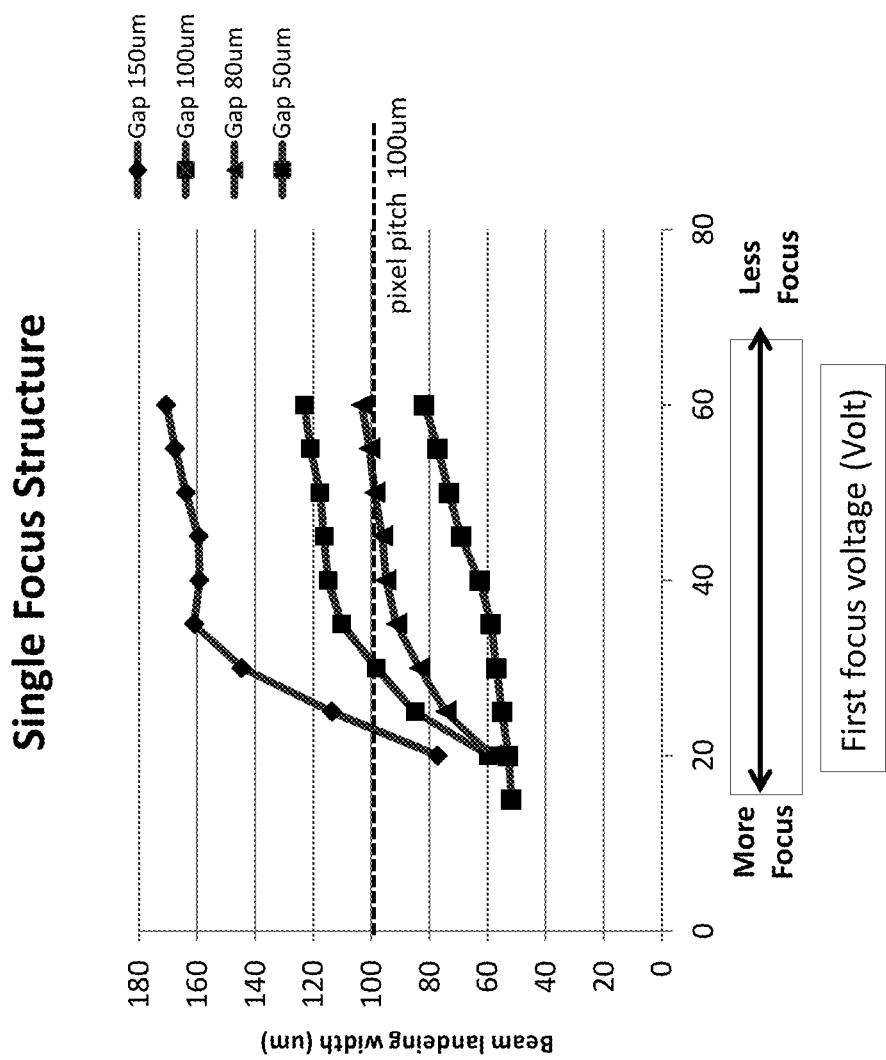
FIG. 13 shows the results of a simulation showing the effect of a single focus structure on electron beam trajectory.

With reference to FIG. 13, the presence of a first focus structure and the application of a first focus voltage across a first focus electrode may restrict the beam landing width.

For example, in a simulated image capture device having an electron emission construct with a single focus structure with a gap (anode to cathode) of 100 micrometers, the beam landing width was restricted to about 100 micrometers, in order to match the target pixel pitch of 100 micrometers, with the application of about 30 volts to the first focus electrode (cathode basis). With a gap of 150 micrometers, the beam landing width was restricted to about 100 micrometers with the application of about 22.5 volts (between 20 and 25 volts) to the first focus electrode. The optimal first focus voltage depends on the size of the gap (e.g., anode to cathode distance), as well as with other of parameters including the specifications of the field emission type electron source, the dimensions of the focus structure, and other parameters of the device, which may be adjusted as needed. The results of the single focus simulation are shown below in Table 1.

TABLE 1

Beam Landing Width (in micrometers) with single focus

| Gap (micrometers) | 1st Focus Voltage | | |
|---|---|---|---|
| | 20 volts | 40 volts | 60 volts |
| 50 | 53 | 62.8 | 81.8 |
| 80 | 58.7 | 95.1 | 103.4 |
| 100 | 59.8 | 115.1 | 123.2 |
| 150 | 77.3 | 159.3 | 170.8 |

It will be appreciated that the effect of the focus structure on beam landing width described above would be same in a simulated x-ray emission device having a similarly configured election emission construct.

Figure 14:
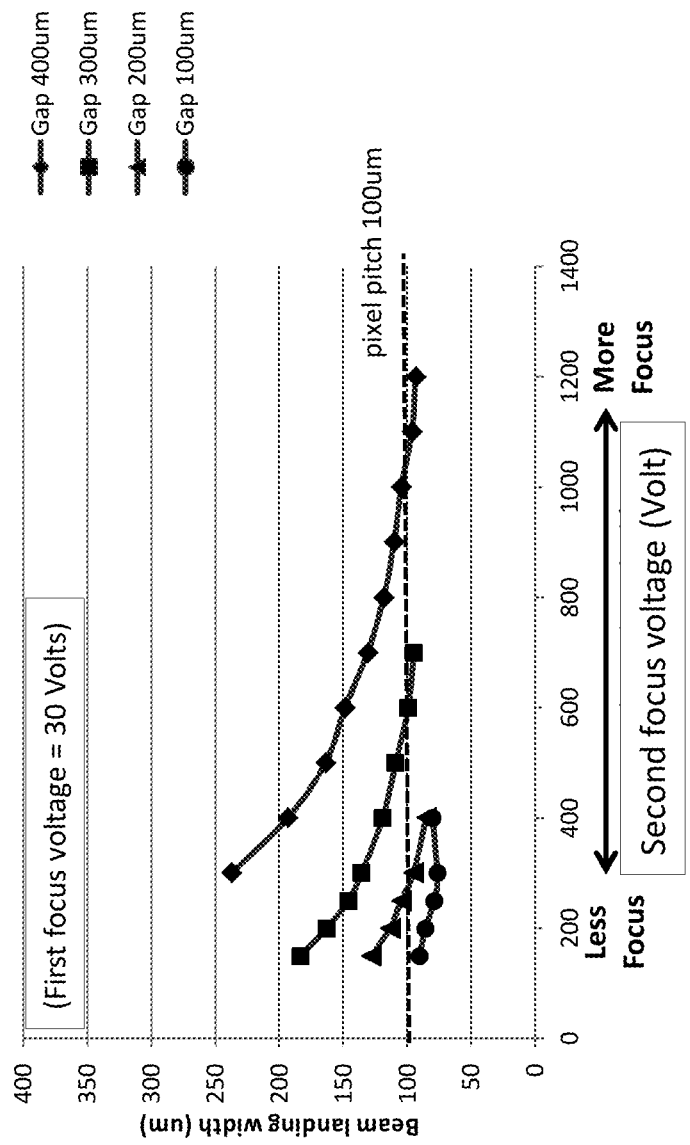
FIG. 14 shows the results of a simulation showing the effect of a double focus structure on electron beam trajectory.

With reference to FIG. 14, the further presence of a second focus structure in combination with the first focus structure (i.e., a double focus) may further restrict the beam landing width. For example, in a simulated image capture device comprising a double focus structure with a gap (anode to cathode) of 300 micrometers, the beam landing width was restricted to about 100 micrometers, in order to match the target pixel pitch of 100 micrometers, with the application of about 600 volts to the second focus electrode (cathode basis) in combination with the application of 30 volts to the first focus electrode (cathode basis). With a gap of 400 micrometers, the beam landing width was restricted to about 100 micrometers with the application of about 1000 volts to the second focus electrode in combination with the application of 30 volts to the first focus electrode. The optimal second focus voltage depends on the size of the gap (e.g., anode to cathode distance), as well as with other of parameters including the specifications of the field emission type electron source, the dimensions of the focus structure, and other parameters of the device, which may be adjusted as needed. The results of the double focus simulation are shown below in Table 2.

TABLE 2

Beam Landing Width (in micrometers) with double focus

| Gap (micrometers) | 2nd Focus Voltage | | | | |
|---|---|---|---|---|---|
| | 200 volts | 400 volts | 600 volts | 800 volts | 1000 volts |
| 100 | 85.9 | 80.4 | | | |
| 200 | 113.5 | 85.5 | | | |
| 300 | 162.9 | 119.1 | 99.4 | | |
| 400 | | 193.3 | 148.7 | 118.5 | 104.7 |

(first focus voltage = 30 volts)

It will be appreciated that the effect of the focus structure on beam landing width described above would be same in a simulated x-ray emission device having a similarly configured election emission construct.

Example 2

The Effect of Electron Initial Velocity on Focal Spot Size

Figure 15:
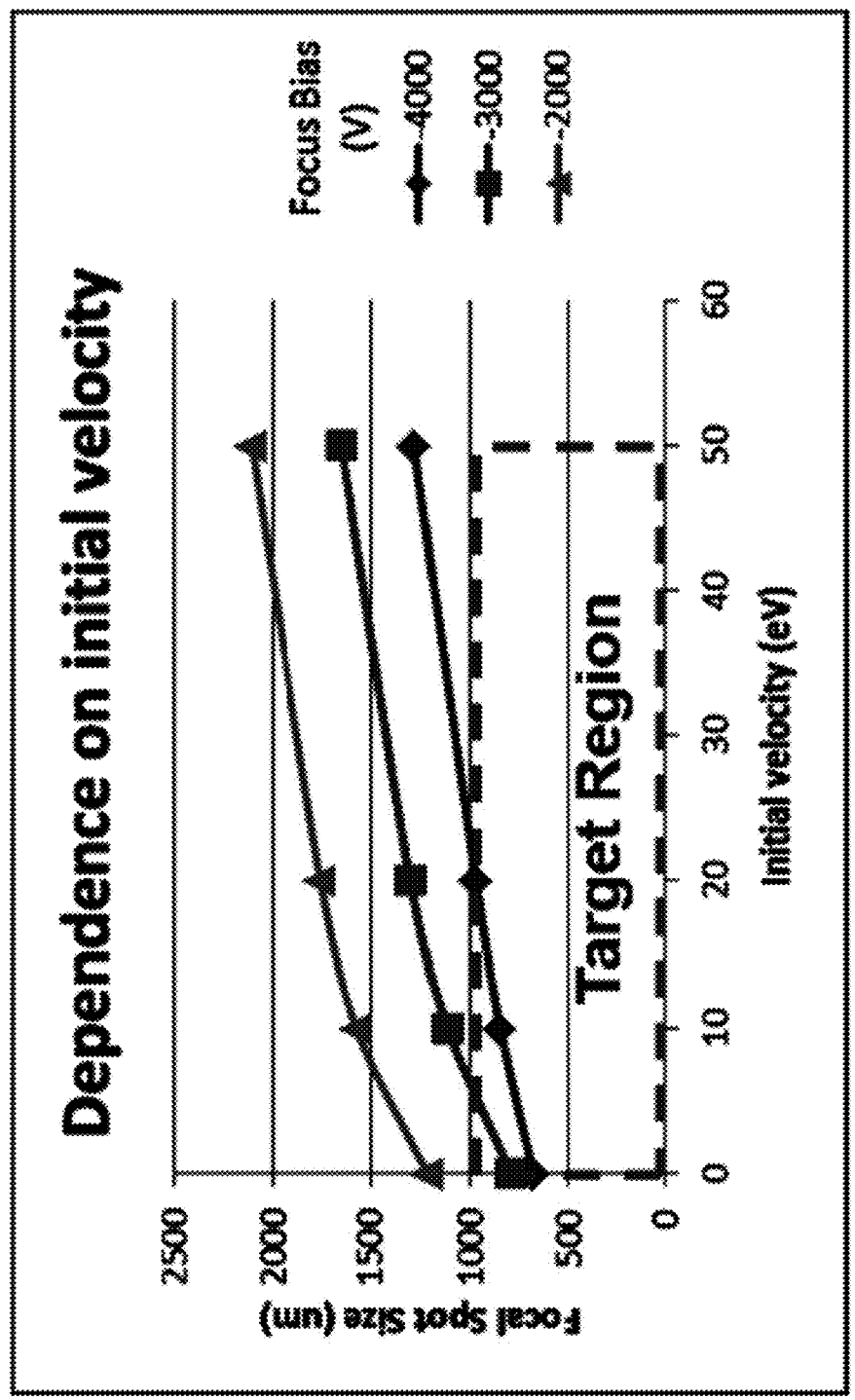
FIG. 15 is a plot showing the results of a simulation showing the effects of initial electron velocity focus bias on focal spot size.

FIG. 15 shows the results of a simulated device having an electron emitting construct and an electron receiving construct (e.g., an image capture device or an x-ray emitting device) depicting how the width of an electron beam, at the point where it strikes an anode facing it (i.e., the focal spot size), increases as the initial electron velocity of the electron beam emitted from a gated cone electron source increases from 0 eV to 50 eV. Given the conditions applied to the simulation (a cathode area of 5 millimeters, the distance between the cathode and the anode being 4 mm, and the focus window (the inner width of the focus structure) being 14 mm, a focal spot size of less than 1000 microns was achieve with an initial electron velocity of 10 eV and a focus bias (the voltage applied to the focus structure) of −4000V.

The scope of the disclosed embodiments may be defined by the appended claims and includes both combinations and sub combinations of the various features described hereinabove as well as variations and modifications thereof, which would occur to persons skilled in the art upon reading the foregoing description.

Technical and scientific terms used herein should have the same meaning as commonly understood by one of ordinary skill in the art to which the disclosure pertains. Nevertheless, it is expected that during the life of a patent maturing from this application many relevant systems and methods will be developed.

As used herein the term "about" refers to at least ±10%.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" may include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be understood, therefore, that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6 as well as non-integral intermediate values. This applies regardless of the breadth of the range.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

The invention claimed is:

1. An x-ray emitting device comprising:
    an x-ray emitting construct, an electron emitting construct, at least one spacer, a voltage source and a gate interconnect lead;
    said at least one spacer situated such that the x-ray emitting construct and the electron emitting construct face each other;
    an evacuated inner gap between said x-ray emitting construct and said electron emitting construct;
    said x-ray emitting construct comprising an anode, the anode being an x-ray target; and
    said electron emitting construct comprising at least one active zone, each of said at least one active zone comprising at least one active area comprising:
        (a) a cathode;
        (b) a gated cone electron source, comprising a plurality of emitter tips arranged in an array;
        (c) a resistive layer situated between the gated cone electron source and the cathode; and
        (d) a gate electrode comprising a plurality of gate holes, the position of at least one of said plurality of gate holes corresponding to the position of at least one of said plurality of emitter tips;
    wherein each of said plurality of emitter tips is configured to emit an electron beam towards the x-ray emitting construct;
    wherein the gate electrode is connected to said voltage source through said gate interconnect lead;
    wherein the resistive layer is characterized by at least one feature selected from:
        the resistive layer is of a thickness greater than 300 nanometer or between 300 and 5000 nanometers;
        the resistive layer comprises SiCN;
        the resistive layer comprising a first barrier sublayer situated at the interface with the cathode; and
        the resistive layer comprising a second barrier sublayer situated at the interface with the gated cone electron source; and
    wherein the first barrier sublayer and the second barrier sublayer are characterized by at least one feature selected from:
        the first barrier sublayer and the second barrier sublayer are comprising SiCN or SiC having a silicon atomic percentage of less than 40%; and
        the first barrier sublayer and the second barrier sublayer are comprising amorphous carbon.

2. The x-ray emitting device of claim 1, wherein a diameter of each of the plurality of gate holes is less than 200 nanometers.

3. The x-ray emitting device of claim 1, wherein the at least one active zone being characterized by at least one feature selected from:
    (a) the at least one active zone comprising more than one active area;
    (b) the at least one active zone is enclosed by at least one focus structure;
    (c) the at least one active zone comprising a plurality of active areas, wherein said plurality of active areas are configured to be co-activated; and
    (d) the at least one active zone comprising a plurality of active areas, wherein one or more subsets of said plurality of active areas are capable of being activated independently.

4. The x-ray emitting device of claim 3, wherein the at least one active area being characterized by at least one feature selected from:
    (a) the at least one active area being of an area of between 100 square microns and 4 square millimeters; and
    (b) the at least one active area comprising between 1 and 10 emitter tips per square micron.

5. The x-ray emitting device of claim 1, wherein the gate electrode being situated in a gap of the gate interconnect lead such that the gate electrode is connected on all sides to the gate interconnect lead.

6. The x-ray emitting device of claim 5, wherein the gate interconnect lead being characterized by at least one feature selected from:
   (a) the gate interconnect lead is thicker than the gate electrode; and
   (b) the gate interconnect lead is of a thickness between 0.5 micron and 20 microns.

7. The x-ray emitting device of claim 1, wherein the cathode is of a thickness between 0.5 micron and 20 microns.

8. The x-ray emitting device of claim 1, further comprising a substrate.

9. The x-ray emitting device of claim 8, wherein at least one member selected from the group consisting of the gate electrode, the cathode, the resistive layer and the gated cone electron source is integral to the substrate.

10. The x-ray emitting device of claim 9, wherein the substrate is silicon-based.

\* \* \* \* \*